United States Patent
Kaneko

(10) Patent No.: US 7,071,170 B2
(45) Date of Patent: *Jul. 4, 2006

(54) MACROLIDE ANTIBIOTICS

(75) Inventor: Takushi Kaneko, Guildford, CT (US)

(73) Assignee: Pfizer Inc., New York, NY (US)

( * ) Notice: Subject to any disclaimer, the term of this patent is extended or adjusted under 35 U.S.C. 154(b) by 7 days.

This patent is subject to a terminal disclaimer.

(21) Appl. No.: 10/896,293

(22) Filed: Jul. 21, 2004

(65) Prior Publication Data

US 2005/0004047 A1 Jan. 6, 2005

Related U.S. Application Data

(63) Continuation of application No. 10/206,652, filed on Jul. 24, 2002, now Pat. No. 6,835,716, which is a continuation of application No. 09/969,486, filed on Oct. 1, 2001, now abandoned, which is a continuation of application No. 09/432,441, filed on Nov. 2, 1999, now abandoned.

(60) Provisional application No. 60/106,836, filed on Nov. 3, 1998.

(51) Int. Cl.
A61K 31/70 (2006.01)
C07H 17/08 (2006.01)

(52) U.S. Cl. .................. 514/29; 536/7.2; 536/7.3; 536/7.4

(58) Field of Classification Search ............ 536/7.2, 536/7.3, 7.4; 514/29
See application file for complete search history.

(56) References Cited

U.S. PATENT DOCUMENTS

| | | | |
|---|---|---|---|
| 4,474,768 A | 10/1984 | Bright | 424/180 |
| 4,517,359 A | 5/1985 | Kobrehel et al. | 536/7.4 |
| 5,332,807 A | 7/1994 | Waddell et al. | 536/7.4 |
| 5,439,889 A | 8/1995 | Agouridas et al. | 514/29 |
| 5,444,051 A | 8/1995 | Agouridas et al. | 514/29 |
| 5,527,780 A | 6/1996 | Agouridas et al. | 514/29 |
| 5,543,400 A | 8/1996 | Agouridas et al. | 514/29 |
| 5,614,614 A | 3/1997 | Agouridas et al. | 536/7.5 |
| 5,629,296 A | 5/1997 | Kujundzic et al. | 514/29 |
| 5,721,346 A | 2/1998 | Lazarevski et al. | 536/17.9 |
| 5,854,219 A | 12/1998 | Kujundzicet al. | 514/29 |
| 5,866,549 A | 2/1999 | Or et al. | 514/29 |
| 6,025,350 A | 2/2000 | Masamune et al. | 514/183 |
| 6,028,181 A | 2/2000 | Or et al. | 536/7.2 |
| 6,043,226 A | 3/2000 | Lundy et al. | 514/29 |
| 6,075,011 A | 6/2000 | Or et al. | 514/29 |
| 6,075,133 A | 6/2000 | Or et al. | 536/7.2 |
| 6,323,232 B1 | 11/2001 | Ke et al. | 514/408 |
| 6,339,063 B1 | 1/2002 | Kropp et al. | 514/29 |
| 6,369,035 B1 | 4/2002 | Kobrehel et al. | 514/29 |
| 6,407,074 B1 | 6/2002 | Bronk et al. | 514/29 |
| 2002/0052328 A1 | 5/2002 | Kaneko et al. | 514/29 |
| 2003/0100518 A1 | 5/2003 | Wu et al. | 514/29 |

FOREIGN PATENT DOCUMENTS

| | | |
|---|---|---|
| CZ | 288554 | 7/1995 |
| EP | 0657464 | 6/1995 |
| EP | 0735041 | 10/1996 |
| EP | 0838470 | 4/1998 |
| EP | 0941998 | 9/1999 |
| EP | 1114826 | 7/2001 |
| EP | 1122261 | 8/2001 |
| RU | 2130936 | 5/1999 |
| RU | 2170739 | 7/2001 |
| WO | WO 9731640 | 9/1997 |
| WO | WO 9801571 | 1/1998 |
| WO | WO 9809978 | 3/1998 |
| WO | WO 9856801 | 12/1998 |
| WO | WO 9920639 | 4/1999 |
| WO | WO 0026224 | 5/2000 |
| WO | WO 03004509 | 1/2003 |

OTHER PUBLICATIONS

International Search Report, WO 00/26224, published May 11, 2000.
*English language family member to CZ288554.
**English language family member to RU 2130936.
***English language family member to RU2170739.
****English language family member to WO 98/09978.

Primary Examiner—Elli Peselev
(74) Attorney, Agent, or Firm—Gregg C. Benson; Frank W. Forman

(57) ABSTRACT

This invention relates to compounds of the formula

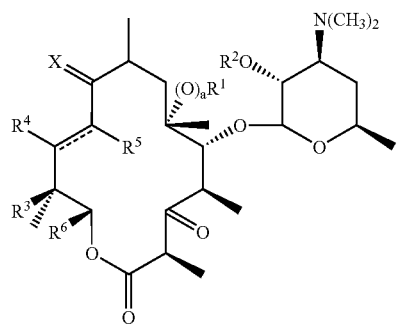

wherein a, $R^1$, $R^2$, $R^3$, $R^4$, $R^5$, $R^6$ and X are each as defined above, and to pharmaceutically acceptable salts thereof, useful as potent antibacterial and antiprotozoal agents that may be used to treat various bacterial and protozoal infections and disorders related to such infections. The invention also relates to pharmaceutical compositions containing the compounds of formula I and to methods of treating bacterial and protozoal infections by administering the compounds of formula I.

14 Claims, No Drawings

MACROLIDE ANTIBIOTICS

This application is a continuation of application Ser. No. 10/206,652 (filed 24 Jul. 2002) now U.S. Pat. No. 6,835,716, which is a continuation of application Ser. No. 09/969,486 (filed 1 Oct. 2001) (abandoned), which is continuation of application Ser. No. 09/432,441 (filed 2 Nov. 1999) (abandoned), which is based on appln. Ser. No. 60/106,836 (filed 3 Nov. 1998). The parent applications are hereby incorporated by reference in their entireities herein.

BACKGROUND OF THE INVENTION

This invention relates to novel macrolide derivatives that are useful as antibacterial and antiprotozoal agents in mammals, including man, as well as in fish and birds. This invention also relates to pharmaceutical compositions containing the novel compounds and to methods of treating bacterial and protozoal infections and disorders related to bacterial infections, such as atherosclerosis and cancer, in mammals, fish and birds by administering the novel compounds to mammals, fish and birds requiring such treatment.

Macrolide antibiotics are known to be useful in the treatment of a broad spectrum of bacterial and protozoal infections in mammals, fish and birds. Such antibiotics include various derivatives of erythromycin A such as azithromycin which is commercially available and is referred to in U.S. Pat. Nos. 4,474,768 and 4,517,359, both of which are incorporated herein by reference in their entirety. Like azithromycin and other macrolide antibiotics, the novel macrolide compounds of the present invention are bond-spectrum macrolide antibodics that are effective against infections caused by certain gram-positive and gram-negative bacteria as well as protozoa.

SUMMARY OF THE INVENTION

The present invention relates to a compound of the formula

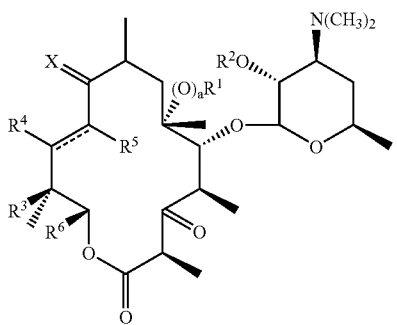

I or the pharmaceutically acceptable salt thereof; wherein the dashed line between positions 10 and 11 represents an optional double bond;

a is 0 or 1;

$R^1$ is hydrogen or $(C_1-C_{10})$alkyl optionally substituted by fluoro, cyano, $R^7$, $R^7 O_2 C$, $R^7 C(O)NH$ and $R^7 S(O)_n$ wherein n is 0, 1 or 2 and $R^7$ is $(C_1-C_6)$alkyl, $(C_2-C_{12})$alkenyl, $(C_2-C_{12})$alkynyl, $(C_3-C_{10})$cycloalkyl$(C_1-C_6)$alkyl, $(C_2-C_9)$heterocycloalkyl$(C_1-C_6)$alkyl, $(C_6-C_{10})$aryl$(C_1-C_6)$alkyl or $(C_2-C_9)$heteroaryl$(C_1-C_6)$alkyl wherein the alkyl, alkenyl, alkynyl, cycloalkyl, heterocycloalkyl, aryl and heteroaryl groups are optionally substituted by one to three halo, $(C_1-C_3)$alkoxy, hydroxy, nitro, cyano, $(C_6-C_{10})$aryl, $(C_2-C_9)$heteroaryl, $R^8R^9N$, $R^8C(O)$, $R^8C(O)O$, $R^8OC(O)$, $R^8C(O)NH$, $R^8NHC(O)$, $R^8R^9NC(O)$ and $R^8OC(O)_2$ wherein $R^8$ and $R^9$ are each independently hydrogen, $(C_1-C_6)$alkyl optionally substituted by $(C_6-C_{10})$aryl or $(C_2-C_9)$heteroaryl;

$R^2$ is hydrogen or a hydroxy protecting group;

$R^3$ is amino, cyano, $N_3$, $R^{10}NH$, $R^{10}C(O)NH$, $R^{10}NHC(O)NH$, $R^{10}NHC(S)NH$, $R^{10}NHNHC(O)NH$, $R^{10}ONHC(O)NH$, $R^{10}O$, $R^{10}OC(O)NH$, $R^{10}S(O)_n$, $R^{10}$phosphoramido, $R^{10}$sulfonamido, SH, $R^{10}S$ wherein n is defined above and $R^{10}$ is $(C_1-C_6)$alkyl, $(C_2-C_{12})$alkenyl, $(C_2-C_{12})$alkynyl, $(C_3-C_{10})$cycloalkyl$(C_1-C_6)$alkyl, $(C_2-C_9)$heterocycloalkyl$(C_1-C_6)$alkyl, $(C_6-C_{10})$aryl, $(C_6-C_{10})$aryl$(C_1-C_6)$alkyl or $(C_2-C_9)$heteroaryl$(C_1-C_6)$alkyl; wherein the alkyl, alkenyl, alkynyl, cycloalkyl, heterocycloalkyl, aryl and heteroaryl groups are optionally substituted by one to three substituents selected independently from halo, $(C_1-C_3)$alkoxy, hydroxy, nitro, cyano, $(C_6-C_{10})$aryl, $(C_2-C_9)$heteroaryl, $R^8R^9N$, $R^8C(O)$, $R^8C(O)O$, $R^8OC(O)$, $R^8C(O)NH$, $R^8NHC(O)$, $R^8R^9NC(O)$ and $R^8OC(O)_2$ wherein $R^8$ and $R^9$ are each independently hydrogen, $(C_1-C_6)$alkyl optionally substituted by $(C_6-C_{10})$aryl or $(C_2-C_9)$heteroaryl; or $R^3$ is $R^{12}R^{13}N$ wherein $R^{12}$ and $R^{13}$ are each independently hydrogen, $(C_1-C_6)$alkyl, $(C_6-C_{10})$aryl$(C_1-C_6)$alkyl or $(C_2-C_9)$heteroaryl $(C_1-C_6)$alkyl;

$R^4$ is hydrogen, methyl optionally substituted by one to two nitro, cyano, $R^{14}C(O)$ and $R^{14}OC(O)$; or $R^4$ is $N_3$, $R^{14}O$, $R^{14}NH$, $R^{14}S$ wherein $R^{14}$ is $(C_1-C_6)$alkyl, $(C_2-C_{12})$alkenyl, $(C_2-C_{12})$alkynyl, $(C_3-C_{10})$cycloalkyl$(C_1-C_6)$alkyl, $(C_2-C_9)$heterocycloalkyl$(C_1-C_6)$alkyl, $(C_6-C_{10})$aryl, $(C_6-C_{10})$aryl$(C_1-C_6)$alkyl or $(C_2-C_9)$heteroaryl$(C_1-C_6)$alkyl; wherein the alkyl, alkenyl, alkynyl, cycloalkyl, heterocycloalkyl, aryl and heteroaryl groups are optionally substituted by one to three substituents independently selected from halo, $(C_1-C_3)$alkoxy, hydroxy, nitro, cyano, $(C_6-C_{10})$aryl, $(C_2-C_9)$heteroaryl, $R^8R^9N$, $R^8C(O)$, $R^8C(O)O$, $R^8OC(O)$, $R^8C(O)NH$, $R^8NHC(O)$, $R^8R^9NC(O)$ and $R^8OC(O)_2$ wherein $R^8$ and $R^9$ are each independently hydrogen, $(C_1-C_6)$alkyl optionally substituted by $(C_6-C_{10})$aryl or $(C_2-C_9)$heteroaryl; or $R^4$ is $R^{15}N(C_1-C_6)$alkyl wherein $R^{15}$ is hydrogen, $(C_1-C_6)$alkyl, $(C_6-C_{10})$aryl$(C_1-C_6)$alkyl or $(C_2-C_9)$heteroaryl$(C_1-C_6)$alkyl;

X is oxygen or $NOR^{16}$ wherein $R_{16}$ is $(C_1-C_6)$alkyl, $(C_2-C_{12})$alkenyl, $(C_2-C_{12})$alkynyl, $(C_3-C_{10})$cycloalkyl$(C_1-C_6)$alkyl, $(C_2-C_9)$heterocycloalkyl$(C_1-C_6)$alkyl, $(C_6-C_{10})$aryl$(C_1-C_6)$alkyl or $(C_2-C_9)$heteroaryl$(C_1-C_6)$alkyl; wherein the alkyl, alkenyl, alkynyl, cycloalkyl, heterocycloalkyl, aryl and heteroaryl groups are optionally substituted by one to three substituents independently selected from halo, $(C_1-C_3)$alkoxy, hydroxy, nitro, cyano, $(C_6-C_{10})$aryl, $(C_2-C_9)$heteroaryl, $R^8R^9N$, $R^8C(O)$, $R^8C(O)O$, $R^8OC(O)$, $R^8C(O)NH$, $R^8NHC(O)$, $R^8R^9NC(O)$ and $R^8OC(O)_2$, wherein $R^8$ and $R^9$ are each independently hydrogen, $(C_1-C_6)$alkyl optionally substituted by $(C_6-C_{10})$aryl or $(C_2-C_9)$heteroaryl;

$R^5$ is hydrogen or methyl;

or $R^3$ and $R^4$ may be taken together with the carbons to which they are attached to form

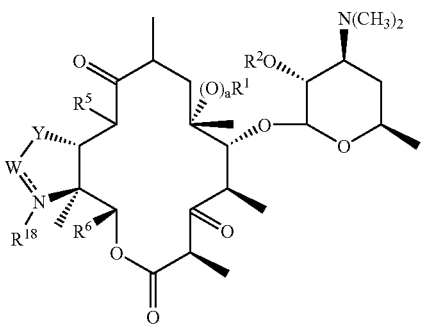

wherein the dashed line, between the nitrogen and the variable W of formula II, represents an optional double bond;

W is C=O, C=S, SO$_2$ or C=NR$^{10}$ wherein R$^{10}$ is as defined above;

Y is oxygen, sulfur or NR$^{17}$ wherein R$^{17}$ is hydrogen, R$^{19}$, R$^{19}$O or R$^{19}$NH wherein R$^{19}$ is hydrogen, $(C_1-C_6)$alkyl, $(C_2-C_{12})$alkenyl, $(C_2-C_{12})$alkynyl, $(C_3-C_{10})$cycloalkyl $(C_1-C_6)$alkyl, $(C_2-C_9)$heterocycloalkyl$(C_1-C_6)$alkyl, $(C_6-C_{10})$aryl, $(C_6-C_{10})$aryl$(C_1-C_6)$alkyl or $(C_2-C_9)$heteroaryl$(C_1-C_6)$alkyl; wherein the alkyl, alkenyl, alkynyl, cycloalkyl, heterocycloalkyl, aryl and heteroaryl groups are optionally substituted by one to three substituents independently selected from halo, $(C_1-C_3)$alkoxy, hydroxy, nitro, cyano, $(C_6-C_{10})$aryl, $(C_2-C_9)$heteroaryl, R$^8$R$^9$N, R$^8$C(O), R$^8$C(O)O, R$^8$OC(O), R$^8$C(O)NH, R$^8$NHC(O), R$^8$R$^9$NC(O) and R$^8$OC(O)$_2$ wherein R$^8$ and R$^9$ are each independently hydrogen, $(C_1-C_6)$alkyl optionally substituted by $(C_5-C_{10})$aryl or $(C_2-C_9)$heteroaryl;

R$^{18}$ is hydrogen, $(C_1-C_6)$alkyl, $(C_6-C_9)$aryl, $(C_6-C_{10})$aryl $(C_1-C_6)$alkyl or $(C_2-C_9)$heteroaryl$(C_1-C_6)$alkyl; wherein the aryl and heteroaryl groups are optionally substituted by one to three substituents independently selected from halo, $(C_1-C_3)$alkoxy, hydroxy, nitro, cyano, $(C_6-C_{10})$aryl, $(C_2-C_9)$heteroaryl, R$^{20}$R$^{21}$N, R$^{20}$OC(O), R$^{20}$C(O)O, R$^{20}$C (O), R$^{20}$C(O)NH, R$^{20}$NHC(O), R$^{20}$R$^{21}$NC(O), and R$^{20}$OCO$_2$ wherein R$^{20}$ and R$^{21}$ are each independently hydrogen, $(C_1-C_6)$alkyl optionally substituted by $(C_6-C_{10})$acyl or $(C_5-C_{10})$aryl; or $(C_2-C_9)$heteroaryl;

R$^6$ is hydrogen, $(C_1-C_6)$alkyl, $(C_2-C_6)$alkenyl, $(C_2-C_6)$alkynyl, $(C_1-C_6)$alkoxy$(C_1-C_6)$alkyl or $(C_1-C_6)$alkylthio $(C_1-C_6)$alkyl wherein the alkyl, alkenyl, alkynyl or alkoxy groups are optionally substituted by one to three substituents independently selected from hydroxy and halo; or R$^6$ is $(C_3-C_{10})$cycloalkyl or $(C_5-C_{10})$cycloalkenyl optionally substituted by $(C_1-C_6)$alkyl or halo; or R$^6$ is $(C_2-C_8)$heterocycloalkyl or $(C_2-C_9)$heteroaryl optionally substituted by $(C_1-C_6)$alkyl, $(C_2-C_8)$alkenyl, $(C_2-C_8)$alkynyl, $(C_3-C_{10})$ cycloalkyl, $(C_5-C_{10})$cycloalkenyl or aryl wherein the aryl group is optionally substituted by alkyl, $(C_1-C_6)$alkoxy or halo;

with the proviso that at least one of R$^{17}$ or R$^{18}$ is hydrogen;

with the proviso that when the dashed line between positions 10 and 11 represents a double bond, R$^4$ is hydrogen; and with the proviso that when a is zero, R$^1$ is hydrogen.

The term "alkyl", as used herein, unless otherwise indicated, includes saturated monovalent hydrocarbon radicals having straight, branched or cyclic moieties. It is understood that for cyclic moieties at least three carbon atoms are required in said alkyl group, and for said alkyl group to include a carbon-carbon double or triple bond at least two carbon atoms are required in said alkyl group.

The term "hydroxy protecting group", as used herein, unless otherwise indicated, includes benzoyl, benzyl, $(C_1-C_6)$alkanoyl, $((C_1-C_3)$alkyl)$_3$silyl, and tert-butyldimethylsilyl groups, preferably an acetyl group. The alkanoyl group can be cleaved after its administration to function as a prodrug.

The term "aryl", as used herein, unless otherwise indicated, includes an organic radical derived from an aromatic hydrocarbon by removal of one hydrogen, such as phenyl or naphthyl.

$(C_2-C_9)$Heterocycloalkyl when used herein refers to pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, chromanyl, etc. One of ordinary skill in the art will understand that the connection of said $(C_2-C_9)$heterocycloalkyl rings is through a carbon or a sp$^3$ hybridized nitrogen heteroatom.

$(C_2-C_9)$Heteroaryl when used herein refers to furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl; etc. One of ordinary skill in the art will understand that the connection of said $(C_2-C_9)$heterocycloalkyl rings is through a carbon atom or a sp$^3$ hybridized nitrogen heteroatom.

The term "acyl", as used herein, unless otherwise indicated, includes a radical of the general formula RCO wherein R is alkyl, alkoxy, aryl, arylalkyl or arylalkyloxy and the terms "alkyl" or "aryl" are as defined above.

The positions of the macrolide derivatives of formula I are defined as follows:

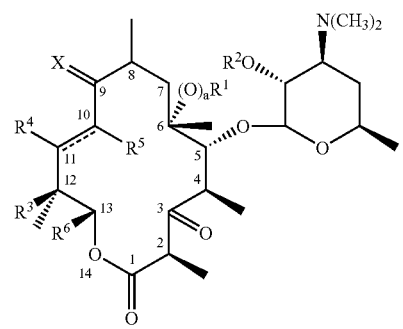

The compounds of this invention include all configurational isomers (e.g., cis and trans isomers) and all optical isomers of compounds of the formula I (e.g., enantiomers and diastereomers), as well as racemic, diastereomeric and other mixtures of such isomers.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include an amino moiety may form pharmaceutically acceptable salts with various amino acids, in addition to the acids mentioned above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

Certain compounds of the present invention may have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them.

The present invention includes the compounds of the present invention, and the pharmaceutically acceptable salts thereof, wherein one or more hydrogen, carbon or other atoms are replaced by isotopes thereof. Such compounds may be useful as research and diagnostic tools in metabolism pharmacokinetic studies and in binding assays.

Preferred compounds of formula I include those wherein a is 1 and $R^1$ is $(C_1–C_{10})$alkyl.

Other preferred compounds of formula I include those wherein $R^2$ is hydrogen.

Other preferred compounds of formula I include those wherein $R^3$ is $N_3$, $R^{10}NH$, $R^{10}C(O)$, $R^{10}NHC(O)NH$ or $R^{10}NHNHC(O)NH$.

Other preferred compounds of formula I include those wherein $R^4$ is hydrogen, $R^{14}NH$ or $R^{14}S$.

Other preferred compounds of formula I include those wherein $R^6$ is ethyl.

Other preferred compounds of formula I include those wherein W is C=O and Y is $NR^{17}$.

More preferred compounds of formula I include those wherein a is 1; $R^1$ is $(C_1–C_{10})$ alkyl; $R^2$ is hydrogen; $R^3$ is $N_3$, $R^{10}NH$, $R^{10}C(O)$, $R^{10}NHC(O)NH$ or $R^{10}NHNHC(O)NH$; $R^4$ is hydrogen, $R^{14}NH$ or $R^{14}S$ and $R^6$ is ethyl.

More preferred compounds of formula I include those wherein a is 1; $R^1$ is $(C_1–C_{10})$alkyl; $R^2$ is hydrogen; $R^3$ and $R^4$ are taken together with the carbons to which they are attached to form the compound of formula II; W is C=O and Y is $NR^{17}$.

Specific preferred compounds of formula I include the following:

11,12-Dideoxy-3-de((2,6-dideoxy-3-C-methyl-3-O-methyl-α-L-ribohexopyranosyl)oxy)-6-O-methyl-12,11-(iminocarbonyl(2-(3-(4-quinolinyl)propyl)hydrazono)-3-oxoerythromycin;

11,12-Dideoxy-10,11-didehydro-3-de((2,6-dideoxy-3-C-methyl-3-O-methyl-α-L-ribohexopyranosyl)oxy)-6-O-methyl-12-iminocarbonyl((4-(4-(3-pyridinyl)-1H-imidazol-1-yl)butylimino)-3-oxoerythromycin;

11,12-Dideoxy-11,12-didehydro-3-de((2,6-dideoxy-3-C-methyl-3-O-methyl-α-L-ribohexopyrano-5yl)oxy-6-O-methyl-10-iminocarbonyl((4-(4-(3-pyridinyl)-1H-imidazol-1-yl)butylimino))-3-oxoerythromycin;

11-Deoxy-10,11-didehydro-3-de((2,6-dideoxy-3-C-methyl-3-O-methyl-α-L-ribohexopyranosyl)oxy)-6-O-methyl-3-oxoerythromycin-1,2-enol-1,12-cyclicether-2'-acetate;

11-Deoxy-10,11-didehydro-3-de((2,6-dideoxy-3-C-methyl-3-O-methyl-3-O-methyl-α-L-ribohexopyranosyl)oxy)-6-O-methyl-8-epi-3-oxoerythromycin-1,2-enol-1,12-cyclicether-2'-acetate;

11,12-Dideoxy-10,11-didehydro-3-de((2,6-dideoxy-3-C-methyl-3-O-methyl-3-O-methyl-α-L-ribohexopyranosyl)oxy)-12-β-azido-O-methyl-3-oxoerythromycin-2'-acetate;

11,12-Dideoxy-10,11-didehydro-3-de((2,6-dideoxy-3-C-methyl-3-O-methyl-α-L-rihexopyranosyl)oxy)-12-β-azido-6-O-methyl-3-oxo-8-epierythromycin-2'-acetate;

11,12-Dideoxy-10,11-didehydro-3-de((2,6-dideoxy-3-C-methyl-3-O-methyl-α-L-ribohexopyranosyl)oxy)-12-β-amino-6-O-methyl-3-oxoerythromycin-2'-acetate;

11,12-Dideoxy-10,11-didehydro-3-de((2,6-dideoxy-3-C-methyl-3-O-methyl-α-L-ribohexopyranosyl)oxy)-12-β-amino-6-O-methyl-3-oxo-8-erythromycin-2'-acetate;

11,12-Dideoxy-10,11-didehydro-3-de((2,6-dideoxy-3-C-methyl-α-L-ribohexopyranosyl)oxy)-12-β-acetamino-6-O-methyl-3-oxoerythromycin-2'acetate;

11,12-Dideoxy-11,12-dehydro-3-de((2,6-dideoxy-3-C-methyl-3-O-methyl-α-L-ribohexopyranosyl)oxy)-10-β-azido-6-O-methyl-3-oxoerythromycin-2'-acetate;

11,12-Dideoxy-11,12-dehydro-3-de((2,6-dideoxy-3-C-methyl-3-O-methyl-α-L-ribohexopyranosyl)oxy)-10-β-amino-6-O-methyl-3-oxoerythromycin-2'-acetate;

11,12-Dideoxy-11,12-dehydro-3-de((2,6-dideoxy-3-C-methyl-3-O-methyl-α-L-ribohexopyranosyl)oxy)-10-β-acetamino-6-O-methyl-3-oxoerythromycin-2'-acetate;

11,12-Dideoxy-3-de((2,6-dideoxy-3-C-methyl-3-O-methyl-α-L-ribohexopyranosyl)oxy)-6-O-methyl-3-oxo-12,11-(iminocarbonylhydrazono)erythromycin-2'-acetate;

11,12-Dideoxy-11,12-dehydro-3-de((2,6-dideoxy-3-C-methyl-3-O-methyl-α-L-ribohexopyranosyl)oxy)-10-β-iminocarbonylhydrazono-6-O-methyl-3-oxo-erythromycin-2'-acetate;

11,12-Dideoxy-10,11-didehydro-3-de((2,6-dideoxy-3-C-methyl-3-O-methyl-α-L-ribohexopyranosyl)oxy)-12-β-isothiocyanato-6-O-methyl-3-oxoerythromycin-2'-acetate;

11,Deoxy-10,11-didehydro-3-de((2,6-dideoxy-3-C-methyl-3-O-methyl-α-L-ribohexopyranosyl)oxy)-12-β-propagyloxy-6-O-methyl-3-oxoerythromycin-2'-acetate;

11-Deoxy-10,11-didehydro-3-de((2,6-dideoxy-3-C-methyl-3-O-methyl-α-L-ribohexopyranosyl)oxy)-6-O-methyl-11-nitromethyl-3-oxoerythromycin-1,2-enol-1,12-cyclicether-2'-acetate; and 11-Deoxy-10,11-didehydro-3-de((2,6-dideoxy-3-C-methyl-3-O-methyl-α-L-ribohexopyranosyl)oxy)-6-methyl-11-nitromethyl-8-epi-3-oxoerythromycin-1,2-enol-1,12-cyclicether-2'-acetate.

The invention also relates to a pharmaceutical composition for the treatment of a disorder selected from a bacterial infection, a protozoal infection, or disorder related to a bacterial infection or protozoal infection in a mammal, fish, or bird which comprises a therapeutically effective amount of a compound of formula I, or a pharmaceutically acceptable salt thereof, and a pharmaceutically acceptable carrier.

The invention also relates to a method of treating a disorder selected from a bacterial infection, a protozoal infection, or disorder related to a bacterial infection or protozoal infection in a mammal, fish, or bird which comprises administering to said mammal, fish or bird a therapeutically effective amount of a compound of formula I or a pharmaceutically acceptable salt thereof.

The invention also relates to a pharmaceutical composition for the treatment of cancer, in particular non-small cell lung cancer, in a mammal, in particular a human, which comprises a therapeutically effective amount of a compound of formula I, or a pharmaceutically acceptable salt thereof, and a pharmaceutically acceptable carrier.

The invention also relates to a method of treating cancer, in particular non-small cell lung cancer, in a mammal, which comprises administering to said mammal a therapeutically effective amount of a compound of formula I or a pharmaceutically acceptable salt thereof.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

As used herein, unless otherwise indicated, the terms or phrases "bacterial infection(s)", "protozoal infection(s)", and "disorder related to a bacterial infection or protozoal infection" include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus*, or *Peptostreptococcus* spp.; pharynigitis, rheumatic fever, and glomerulonephritis related to infection by *Streptococcus pyogenes*, Groups C and G *streptococci, Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive *staphylococci* (i.e., *S. epidermidis, S. hemolyticus*, etc.), *Streptococcus pyogenes, Streptococcus agalactiae*, Streptococcal groups C–F (minute-colony streptococci), *viridans streptococci, Corynebacterium minutissimum, Clostridium* spp., or *Bartonella henselae*; uncomplicated acute urinary tract infections related to infection by *Staphylococcus saprophyticus* or *Enterococcus* spp.; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome), or Groups A, B, and C *streptococci*; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by *Cryptosporidium* spp.; odontogenic infection related to infection by *viridans streptococci;* persistent cough related to infection by *Bordetella pertussis*; gas gangrene related to infection by *Clostridium perfringens* or *Bacteroides* spp.; and atherosclerosis or cardiovascular disease related to infection by *Chlamydia pneumoniae*. Bacterial infections and protozoal infections, and disorders related to such infections, which may be treated or prevented in animals include the following: bovine respiratory disease related to infection by *P. haemolytica, P. muftocida, Mycoplasma bovis*, or *Bordetella* spp.; cow enteric disease related to infection by *E. coli* or protozoa (i.e., *coccidia, cryptosporidia*, etc.); dairy cow mastitis related to infection by *Staph. aureus, Strep. uberis, Strep. agalactiae, Strep. dysgalactiae, Kdebsiella* spp., *Corynebacterium*, or *Enterococcus* spp.; swine respiratory disease related to infection by *A. pleuro., P. multocida*, or *Mycoplasma* spp.; swine enteric disease related to infection by *E. coli, Lawsonia intracellularis, Salmonella*, or *Serpulina hyodysinteriae*; cow footrot related to infection by *Fusobactedium* spp.; cow metritis related to infection by *E. coli*; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *E. coli*; skin and soft tissue infections in dogs and cats related to infection by *Staph. epidermidis, Staph. intermedius, coagulase neg. Staph.* or *P. multocida*; and dental or mouth infections in dogs and cats related to infection by *Alcaligenes* spp., *Bacteroides* spp., *Clostridium* spp., *Enterobacter* spp., *Eubacterium, Peptostreptococcus, Porphyromonas*, or *Prevotella*. Other bacterial infections and protozoal infections, and disorders related to such infections, which may be treated or prevented in accord with the method of the present invention are referred to in J. P. Sanford et al., "The Sanford Guide To Antimicrobial Therapy," 26th Edition, (Antimicrobial Therapy, Inc., 1996).

The present invention also relates to a compound of the formula

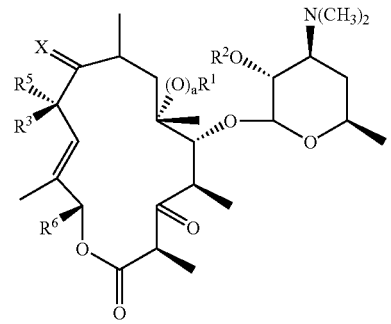

XXXXI or the pharmaceutically acceptable salt thereof; wherein the dashed line between positions 10 and 11 represents an optional double bond;

a is 0 or 1;

$R^1$ is hydrogen or $(C_1–C_{10})$alkyl optionally substituted by fluoro, cyano, $R^7$, $R^7O_2C$, $R^7C(O)NH$ and $R^7S(O)_n$ wherein n is 0, 1 or 2 and $R^7$ is $(C_1-C_6)$alkyl, $(C_2-C_{12})$alkenyl, $(C_2-C_{12})$alkynyl, $(C_3-C_{10})$cycloalkyl$(C_1-C_6)$alkyl, $(C_2-C_9)$heterocycloalkyl$(C_1-C_6)$alkyl, $(C_6-C_{10})$aryl$(C_1-C_6)$alkyl or $(C_2-C_9)$heteroaryl$(C_1-C_6)$alkyl wherein the alkyl, alkenyl, alkynyl, cycloalkyl, heterocycloalkyl, aryl and heteroaryl groups are optionally substituted by one to three substituents independently selected from halo, $(C_1-C_3)$alkoxy, hydroxy, nitro, cyano, $(C_6-C_{10})$aryl, $(C_2-C_9)$heteroaryl, $R^8R^9N$, $R^8C(O)$, $R^8C(O)O$, $R^8OC(O)$, $R^8C(O)NH$, $R^8NHC(O)$, $R^8R^9NC(O)$ and $R^8OC(O)_2$ wherein $R^8$ and $R^9$ are each independently hydrogen, $(C_1-C_6)$alkyl optionally substituted by $(C_6-C_{10})$aryl or $(C_2-C^9)$heteroaryl;

$R^2$ is hydrogen or a hydroxy protecting group;

$R^3$ is $N_3$, $R^{10}NH$, $R^{10}C(O)NH$, $R^{10}NHC(O)NH$, $R^{10}NHC(S)NH$, $R^{10}NHNHC(O)NH$, $R^{10}ONHC(O)NH$ or $R^{10}OC(O)NH$, wherein $R^{10}$ is $(C_1-C_6)$alkyl, $(C_2-C_{12})$alkenyl, $(C_2-C_{12})$alkynyl, $(C_3-C_{10})$cycloalkyl$(C_1-C_6)$alkyl, $(C_2-C_9)$heterocycloalkyl$(C_1-C_6)$alkyl, $(C_6-C_{10})$aryl, $(C_6-C_{10})$aryl$(C_1-C_6)$alkyl or $(C_2-C_9)$heteroaryl$(C_1-C_6)$alkyl; wherein the alkyl, alkenyl, alkynyl, cycloalkyl, heterocycloalkyl, aryl and heteroaryl groups are optionally substituted by one to three substituents independently selected from halo, $(C_1-C_3)$alkoxy, hydroxy, nitro, cyano, $(C_6-C_{10})$aryl, $(C_2-C_9)$heteroaryl, $R^8R^9N$, $R^8C(O)$, $R^8C(O)O$, $R^8OC(O)$, $R^8C(O)NH$, $R^8NHC(O)$, $R^8R^9NC(O)$ and $R^8OC(O)_2$ wherein $R^8$ and $R^9$ are each independently hydrogen, $(C_1-C_6)$alkyl optionally substituted by $(C_6-C_{10})$aryl or $(C_2-C_9)$heteroaryl; or $R^3$ is $R^{11}(C_2-C_4)$alkynyl wherein $R^{11}$ is $(C_1-C_6)$alkyl, $(C_6-C_{10})$alkyl$(C_6-C_{10})$aryl$(C_1-C_6)$alkyl or $(C_2-C_9)$heteroaryl$(C_1-C_6)$alkyl; or $R^3$ is $R^{12}R^{13}N$ wherein $R^{12}$ and $R^{13}$ are each independently hydrogen, $(C_1-C_6)$alkyl, $(C_6-C_{10})$aryl$(C_1-C_6)$alkyl or $(C_2-C_9)$heteroaryl$(C_1-C_6)$alkyl;

X is oxygen or $NOR^{16}$ wherein $R^{16}$ is $(C_1-C_6)$alkyl, $(C_2-C_{12})$alkenyl, $(C_2-C_{12})$alkynyl, $(C_3-C_{10})$cycloalkyl$(C_1-C_6)$alkyl, $(C_2-C_9)$heterocycloalkyl$(C_1-C_6)$alkyl, $(C_6-C_{10})$aryl$(C_1-C_6)$alkyl or $(C_2-C_9)$heteroaryl$(C_1-C_6)$alkyl; wherein the alkyl, alkenyl, alkynyl, cycloalkyl, heterocycloalkyl, aryl and heteroaryl groups are optionally substituted by one to three substituents independently selected from halo, $(C_1-C_3)$alkoxy, hydroxy, nitro, cyano, $(C_6-C_{10})$aryl, $(C_2-C_9)$heteroaryl, $R^8R^9N$, $R^8C(O)$, $R^8C(O)O$, $R^8OC(O)$, $R^8C(O)NH$, $R^8NHC(O)$, $R^8R^9NC(O)$ and $R^8OC(O)_2$, wherein $R^8$ and $R^9$ are each independently hydrogen or $(C_1-C_6)$alkyl optionally substituted by $(C_6-C_{10})$aryl or $(C_2-C^9)$ heteroaryl;

$R^5$ is hydrogen or methyl; and $R^6$ is hydrogen, $(C_1-C_6)$alkyl, $(C_2-C_6)$alkenyl, $(C_2-C_6)$alkynyl, $(C_1-C_6)$alkoxy$(C_1-C_6)$alkyl or $(C_1-C_6)$alkylthio$(C_1-C_6)$alkyl wherein the alkyl, alkenyl, alkynyl or alkoxy groups are optionally substituted by one to three substituents independently selected from hydroxy and halo; or $R^6$ is $(C_3-C_{10})$cycloalkyl or $(C_5-C_{10})$cycloalkenyl optionally substituted by $(C_1-C_6)$alkyl or halo; or $R^6$ is $(C_2-C_8)$heterocycloalkyl or $(C_2-C_9)$heteroaryl optionally substituted by $(C_1-C_6)$alkyl, $(C_2-C_8)$alkenyl, $(C_2-C_8)$alkynyl, $(C_3-C_{10})$cycloalkyl, $(C_5-C_{10})$cycloalkenyl or aryl wherein the aryl group is optionally substituted by alkyl, $(C_1-C_6)$alkoxy or halo;

with the proviso that when a is zero, $R^1$ is hydrogen.

The present invention also relates to a compound of the formula

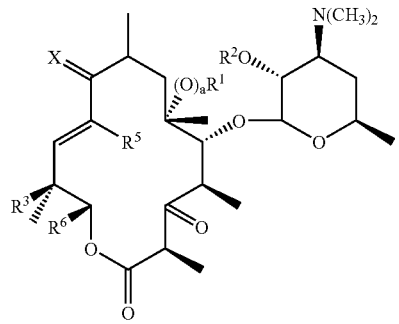

XXXXII a is 0 or 1;

$R^1$ is hydrogen or $(C_1-C_{10})$alkyl optionally substituted by fluoro, cyano, $R^7$, $R^7O_2C$, $R^7C(O)NH$ and $R^7S(O)_n$ wherein n is 0, 1 or 2 and $R^7$ is $(C_1-C_6)$alkyl, $(C_2-C_{12})$alkenyl, $(C_2-C_{12})$alkynyl, $(C_3-C_{10})$cycloalkyl$(C_1-C_6)$alkyl, $(C_2-C_9)$heterocycloalkyl$(C_1-C_6)$alkyl, $(C_6-C_{10})$aryl$(C_1-C_6)$alkyl or $(C_2-C_9)$heteroaryl$(C_1-C_6)$alkyl wherein the alkyl, alkenyl, alkynyl, cycloalkyl, heterocycloalkyl, aryl and heteroaryl groups are optionally substituted by one to three halo, $(C_1-C_3)$alkoxy, hydroxy, nitro, cyano, $(C_6-C_{10})$aryl, $(C_2-C_9)$heteroaryl, $R^8R^9N$, $R^8C(O)$, $R^8C(O)O$, $R^8OC(O)$, $R^8C(O)NH$, $R^8NHC(O)$, $R^8R^9NC(O)$ and $R^8OC(O)_2$ wherein $R^8$ and $R^9$ are each independently hydrogen, $(C_1-C_6)$alkyl optionally substituted by $(C_6-C_{10})$aryl or $(C_2-C_9)$heteroaryl;

$R^2$ is hydrogen or a hydroxy protecting group;

$R^3$ is $NH_2$, $N_3$, $O=C=N$ or $S=C=N$;

X is oxygen or $NOR^{16}$ wherein $R^{16}$ is $(C_1-C_6)$alkyl, $(C_2-C_{12})$alkenyl, $(C_2-C_{12})$alkynyl, $(C_3-C_{10})$cycloalkyl$(C_1-C_6)$alkyl, $(C_2-C_9)$heterocycloalkyl$(C_1-C_6)$alkyl, $(C_6-C_{10})$aryl$(C_1-C_6)$alkyl or $(C_2-C_9)$heteroaryl$(C_1-C_6)$alkyl; wherein the alkyl, alkenyl, alkynyl, cycloalkyl, heterocycloalkyl, aryl and heteroaryl groups are optionally substituted by one to three substituents independently selected from halo, $(C_1-C_3)$alkoxy, hydroxy, nitro, cyano, $(C_6-C_{10})$aryl, $(C_2-C_9)$heteroaryl, $R^8R^9N$, $R^8C(O)$, R C(O)O, $R^8OC(O)$, $R^8C(O)NH$, $R^8NHC(O)$, $R^8R^9NC(O)$ and $R^8OC(O)_2$, wherein $R^8$ and $R^9$ are each independently hydrogen or $(C_1-C_6)$alkyl optionally substituted by $(C_6-C_{10})$aryl or $(C_2-C_9)$heteroaryl;

$R^5$ is hydrogen or methyl; and $R^6$ is hydrogen, $(C_1-C_6)$alkyl, $(C_2-C_6)$alkenyl, $(C_2-C_6)$alkynyl, $(C_1-C_6)$alkoxy$(C_1-C_6)$alkyl or $(C_1-C_6)$alkylthio$(C_1-C_6)$alkyl wherein the alkyl, alkenyl, alkynyl or alkoxy groups are optionally substituted by one to three hydroxy or halo groups; or $R^6$ is $(C_3-C_{10})$cycloalkyl or $(C_5-C_{10})$cycloalkenyl optionally substituted by $(C_1-C_6)$alkyl or halo; or $R^6$ is $(C_2-C_8)$heterocycloalkyl or $(C_2-C_9)$heteroaryl optionally substituted by $(C_1-C_6)$alkyl, $(C_2-C_8)$alkenyl, $(C_2-C_8)$alkynyl, $(C_3-C_{10})$cycloalkyl, $(C_5-C_{10})$cycloalkenyl or aryl wherein the aryl group is optionally substituted by alkyl, $(C_1-C_6)$alkoxy or halo.

The present invention also relates to an intermediate compound of the formula

XXXXIII

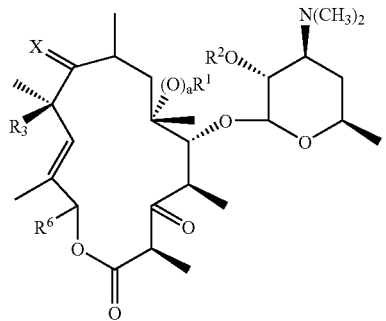

a is 0 or 1;

$R^1$ is hydrogen or $(C_1–C_{10})$alkyl optionally substituted by fluoro, cyano, $R^7$, $R^7O_2C$, $R^7C(O)NH$ and $R^7S(O)_n$ wherein n is 0, 1 or 2 and $R^7$ is $(C_1–C_6)$alkyl, $(C_2–C_{12})$alkenyl, $(C_2–C_{12})$alkynyl, $(C_3–C_{10})$cycloalkyl$(C_1–C_6)$alkyl, $(C_2–C_9)$heterocycloalkyl$(C_1–C_6)$alkyl, $(C_6–C_{10})$aryl$(C_1–C_6)$alkyl or $(C_2–C_9)$heteroaryl$(C_1–C_6)$alkyl wherein the alkyl, alkenyl, alkynyl, cycloalkyl, heterocycloalkyl, aryl and heteroaryl groups are optionally substituted by one to three halo, $(C_1–C_3)$alkoxy, hydroxy, nitro, cyano, $(C_6–C_{10})$aryl, $(C_2–C_9)$heteroaryl, $R^8R^9N$, $R^8C(O)$, $R^8C(O)O$, $R^8OC(O)$, $R^8C(O)NH$, $R^8NHC(O)$, $R^8R^9NC(O)$ and $R^8OC(O)_2$ wherein $R^8$ and $R^9$ are each independently hydrogen, $(C_1–C_6)$alkyl optionally substituted by $(C_6–C_{10})$aryl or $(C_2–C_9)$heteroaryl;

$R^2$ is hydrogen or a hydroxy protecting group;

$R^3$ is $NH_2$ or $N_3$;

X is oxygen or $NOR^{16}$ wherein $R^{16}$ is $(C_1–C_6)$alkyl, $(C_2–C_{12})$alkenyl, $(C_2–C_{12})$alkynyl, $(C_3–C_{10})$cycloalkyl $(C_1–C_6)$alkyl, $(C_2–C_9)$heterocycloalkyl$(C_1–C_6)$alkyl, $(C_6–C_{10})$aryl$(C_1–C_6)$alkyl or $(C_2–C_9)$heteroaryl$(C_1–C_6)$alkyl; wherein the alkyl, alkenyl, alkynyl, cycloalkyl, heterocycloalkyl, aryl and heteroaryl groups are optionally substituted by one to three substituents independently selected from halo, $(C_1–C_3)$alkoxy, hydroxy, nitro, cyano, $(C_6–C_{10})$aryl, $(C_2–C_9)$heteroaryl, $R^8R^9N$, $R^8C(O)$, $R^8C(O)O$, $R^8OC(O)$, $R^8C(O)NH$, $R^8NHC(O)$, $R^8R^9NC(O)$ and $R^8OC(O)_2$, wherein $R^8$ and $R^9$ are each independently hydrogen or $(C_1–C_6)$alkyl optionally substituted by $(C_6–C_{10})$aryl or $(C_2–C_9)$heteroaryl;

$R^5$ is hydrogen or methyl; and $R^6$ is hydrogen, $(C_1–C_6)$alkyl, $(C_2–C_6)$alkenyl, $(C_2–C_6)$alkynyl, $(C_1–c_6)$alkoxy$(C_1–C_6)$alkyl or $(C_1–C_6)$alkylthio $(C_1–C_6)$alkyl wherein the alkyl, alkenyl, alkynyl or alkoxy groups are optionally substituted by one to three substituents independently selected from hydroxy and halo; or $R^6$ is $(C_3–C_{10})$cycloalkyl or $(C_5–C_{10})$cycloalkenyl optionally substituted by $(C_1–C_6)$alkyl or halo; or $R^6$ is $(C_2–C_8)$heterocycloalkyl or $(C_2–C_9)$heteroaryl optionally substituted by $(C_1–C_6)$alkyl, $(C_2–C_8)$alkenyl, $(C_2–C_8)$alkynyl, $(C_3–C_{10})$ cycloalkyl, $(C_5–C_{10})$cycloalkenyl or aryl wherein the aryl group is optionally substituted by alkyl, $(C_1–C_6)$alkoxy or halo.

The present invention also relates to a compound of the formula

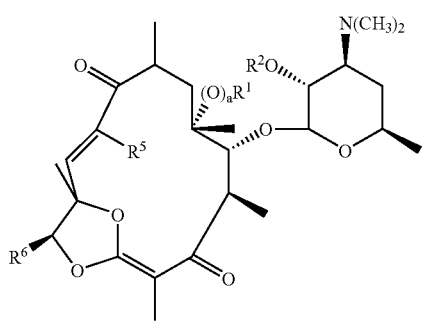

VI a is 0 or 1;

$R^1$ is hydrogen or $(C_1–C_{10})$alkyl optionally substituted by fluoro, cyano, $R^7$, $R^7O_2C$, $R^7C(O)NH$ and $R^7S(O)_n$ wherein n is 0, 1 or 2 and $R^7$ is $(C_1–C_6)$alkyl, $(C_2–C_{12})$alkenyl, $(C_2–C_{12})$alkynyl, $(C_3–C_{10})$cycloalkyl$(C_1–C_6)$alkyl, $(C_2–C_9)$heterocycloalkyl$(C_1–C_6)$alkyl, $(C_6–C_{10})$aryl$(C_1–C_6)$alkyl or $(C_2–C_9)$heteroaryl$(C_1–C_6)$alkyl wherein the alkyl, alkenyl, alkynyl, cycloalkyl, heterocycloalkyl, aryl and heteroaryl groups are optionally substituted by one to three halo, $(C_1–C_3)$alkoxy, hydroxy, nitro, cyano, $(C_6–C_{10})$aryl, $(C_2–C_9)$heteroaryl, $R^8R^9N$, $R^8C(O)$, $R^8C(O)O$, $R^8OC(O)$, $R^8C(O)NH$, $R^8NHC(O)$, $R^8R^9NC(O)$ and $R^8OC(O)_2$ wherein $R^8$ and $R^9$ are each independently hydrogen, $(C_1–C_6)$alkyl optionally substituted by $(C_6–C_{10})$aryl or $(C_2–C_9)$heteroaryl;

$R^2$ is hydrogen or a hydroxy protecting group;

$R^5$ is hydrogen or methyl; and $R^6$ is hydrogen, $(C_1–C_6)$alkyl, $(C_2–C_6)$alkenyl, $(C_2–C_6)$alkynyl, $(C_1–C_6)$alkoxy$(C_1–C_6)$alkyl or $(C_1–C_6)$alkylthio $(C_1–C_6)$alkyl wherein the alkyl, alkenyl, alkynyl or alkoxy groups are optionally substituted by one to three substituents independently selected from hydroxy and halo; or $R^6$ is $(C_3–C_{10})$cycloalkyl or $(C_5–C_{10})$cycloalkenyl optionally substituted by $(C_1–C_6)$alkyl or halo; or $R^6$ is $(C_2–C_8)$heterocycloalkyl or $(C_2–C_9)$heteroaryl optionally substituted by $(C_1–C_6)$alkyl, $(C_2–C_8)$alkenyl, $(C_2–C_8)$alkynyl, $(C_3–C_{10})$ cycloalkyl, $(C_5–C_{10})$cycloalkenyl or aryl wherein the aryl group is optionally substituted by alkyl, $(C_1–C_6)$alkoxy or halo.

DETAILED DESCRIPTION OF THE INVENTION

The following reaction Schemes illustrate the preparation of the compounds of the present invention. Unless otherwise indicated a, $R^1$, $R^2$, $R^3$, $R^4$, $R^5$ and $R^6$ in the reaction Schemes and the discussion that follow are defined as above.

Preparation A
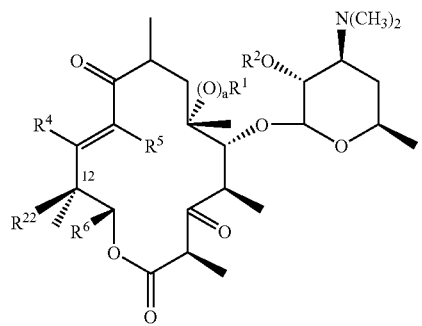
VII
↓ 1
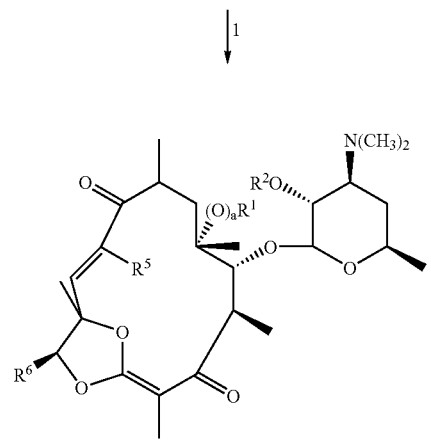
VI
↓ 2
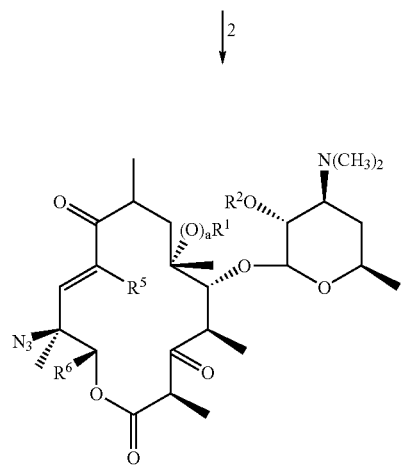
V
↙ 3   ↘ 5

-continued
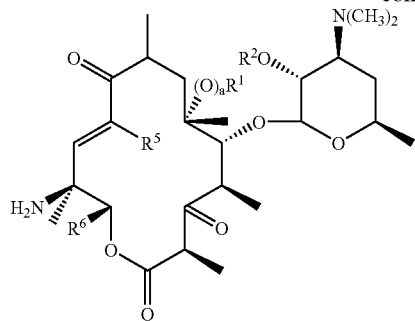
IV
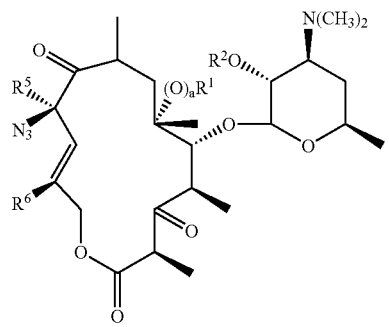
IX
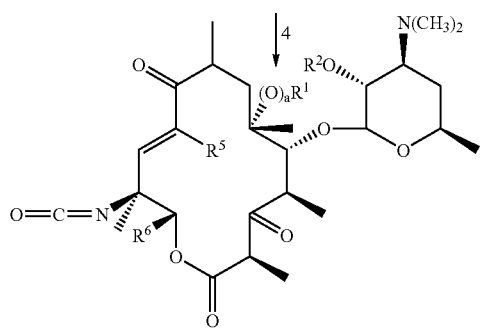
XXII
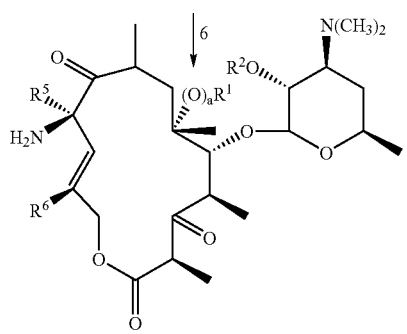
VIII
Preparation B
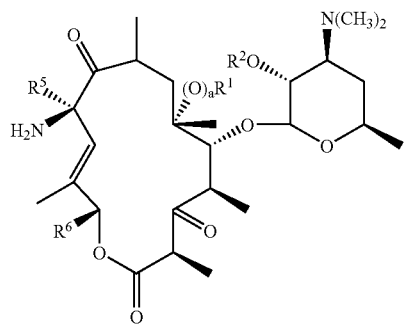
VIII
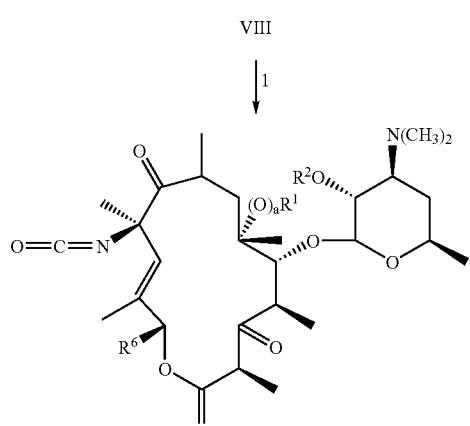
XIII
Preparation C
VI
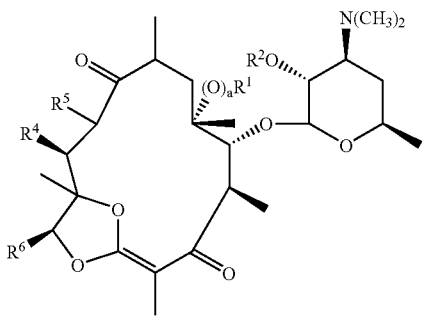
XXXIX

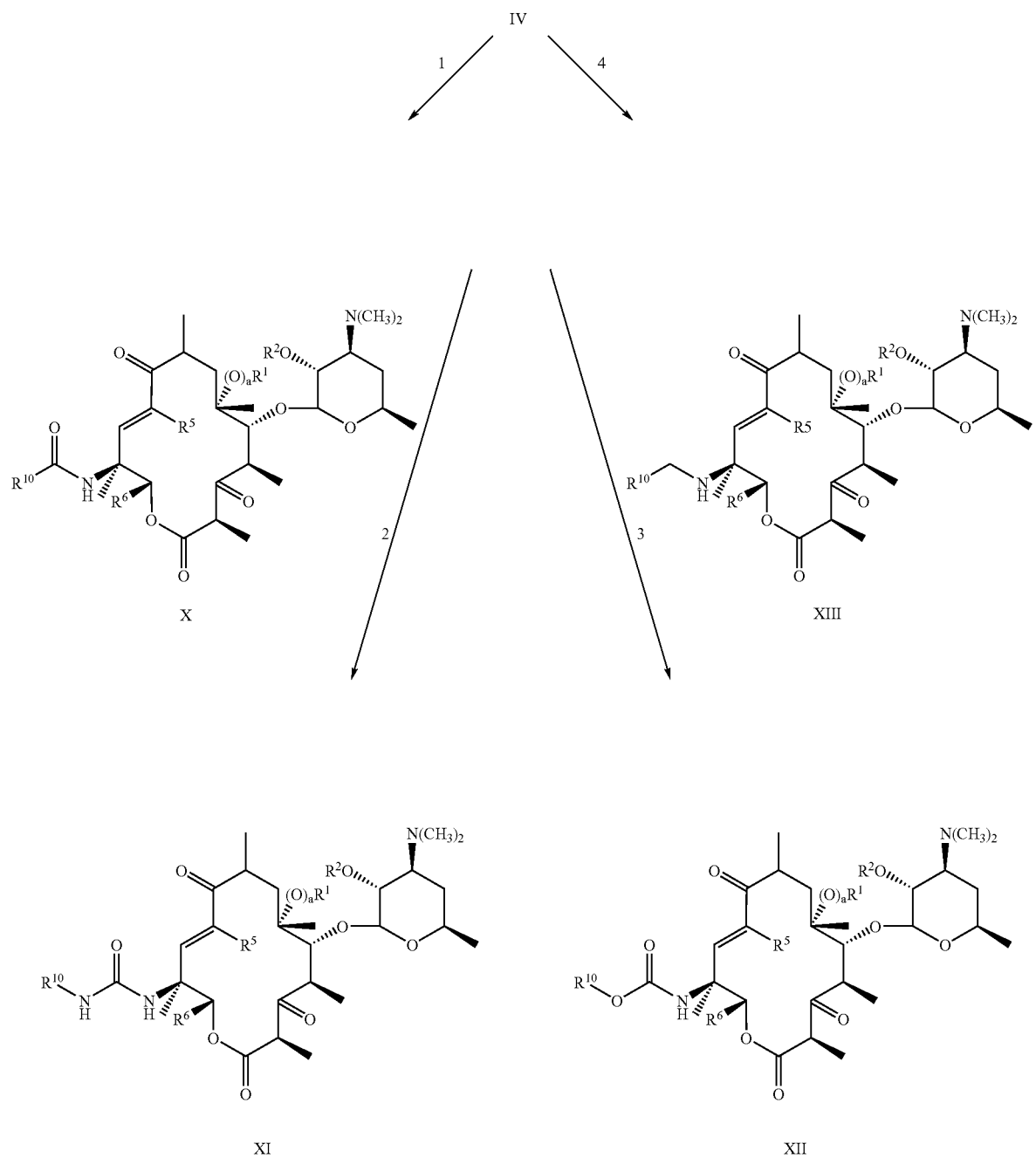
Scheme 1
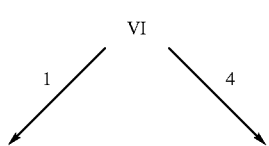
Scheme 2

-continued
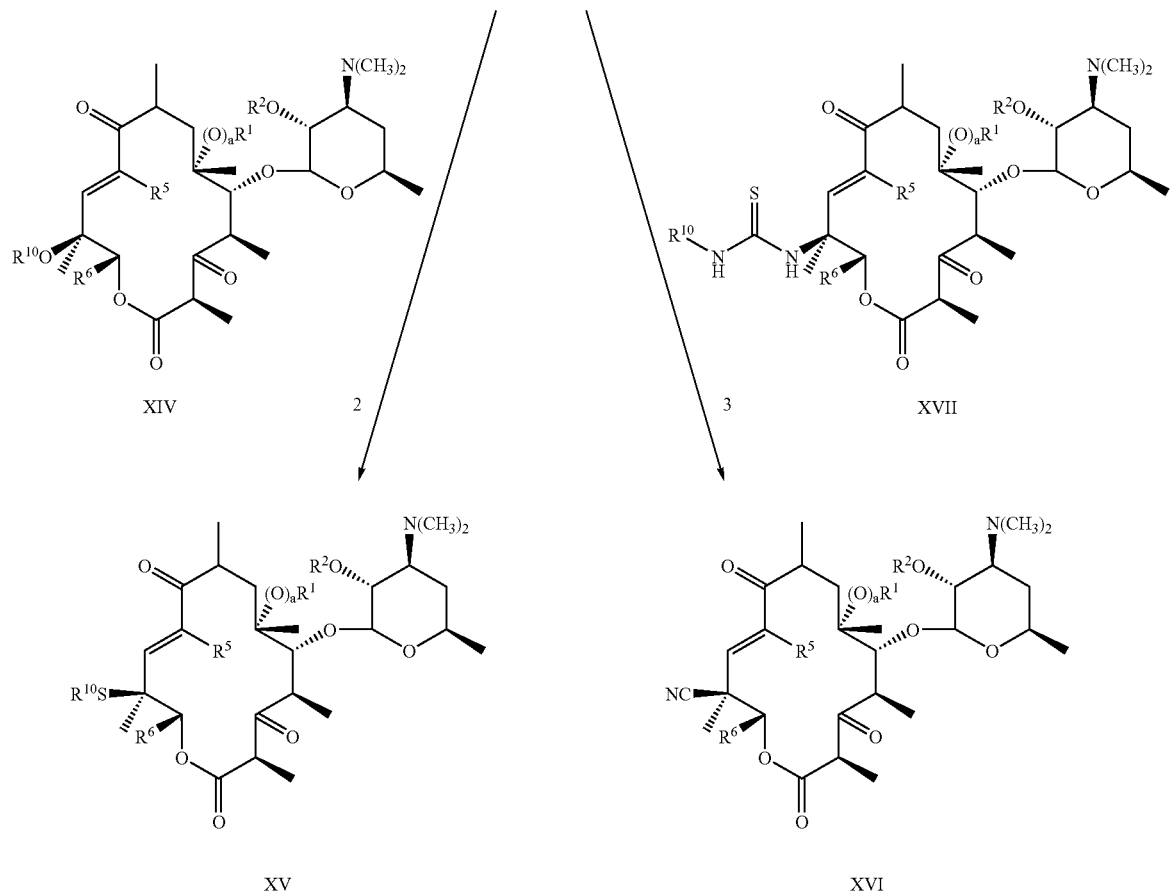
Scheme 3
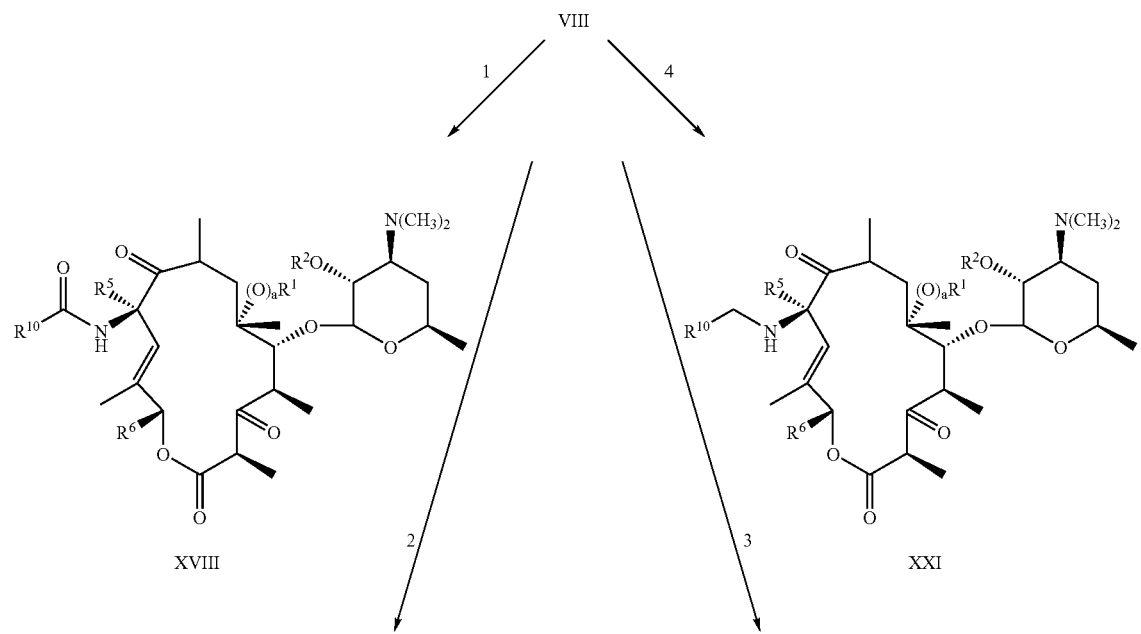

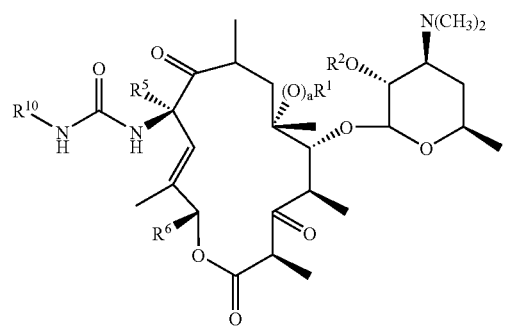
XIX
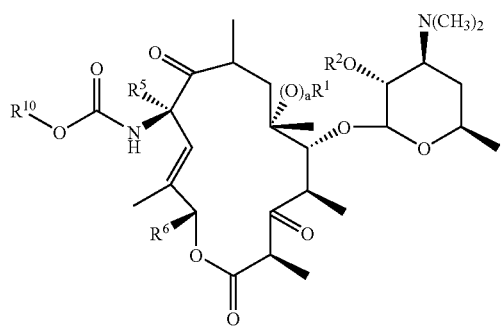
XX
Scheme 4
XXII
↓ 1
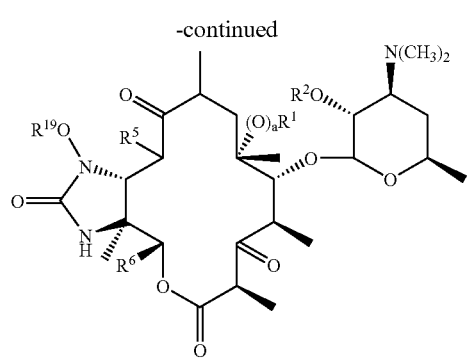
XXIV
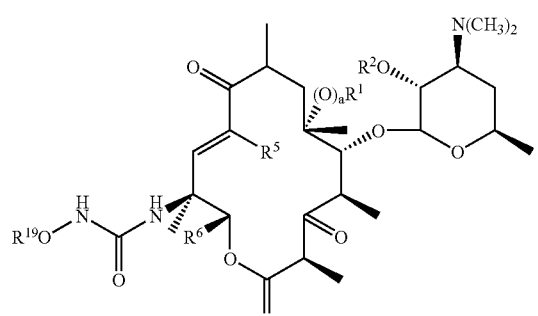
XXIII
↓ 2
Scheme 5
XI
↓ 1
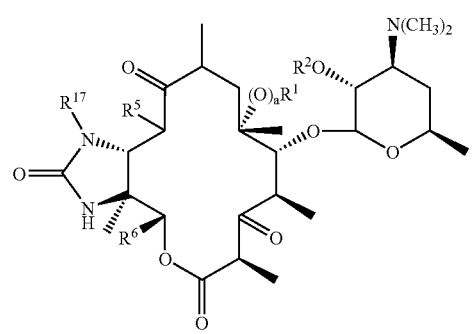
XXV Scheme 6
VI
↓ 1
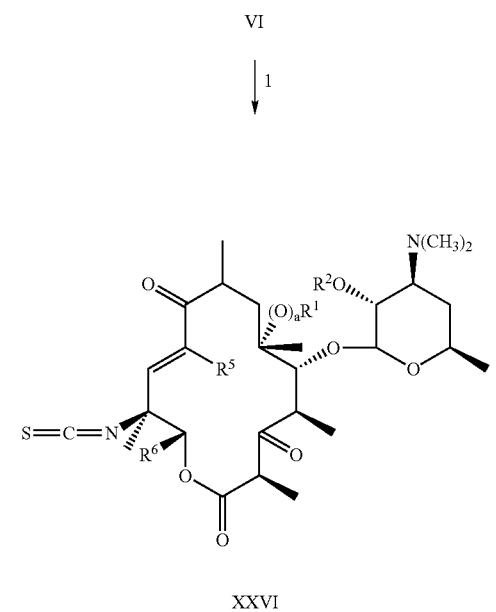
XXVI
↓ 2
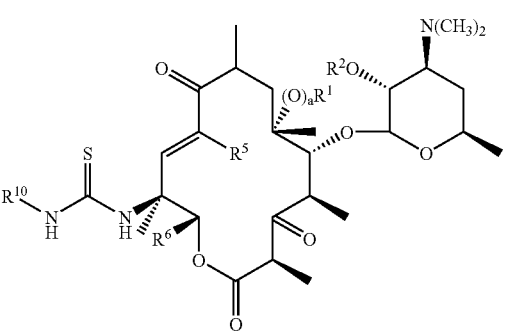
XXVII
↓ 3
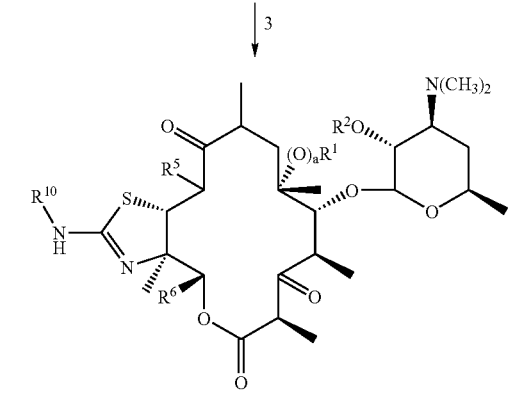
XXVIII
Scheme 7
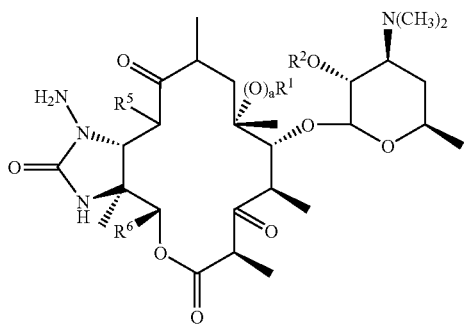
XXIX
↓ 1
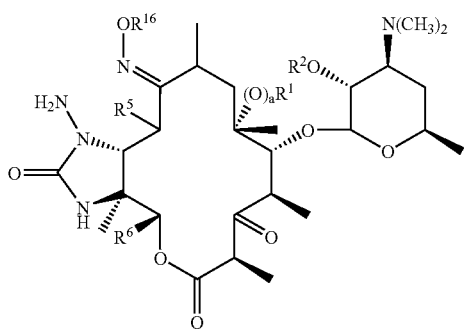
XXX
↓ 2
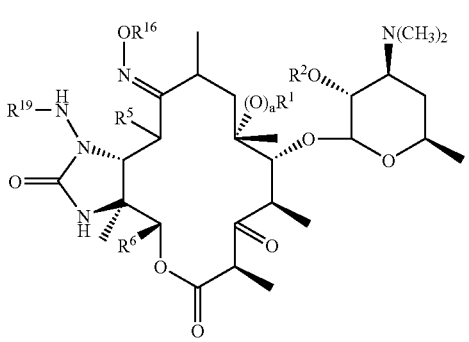
XXXI

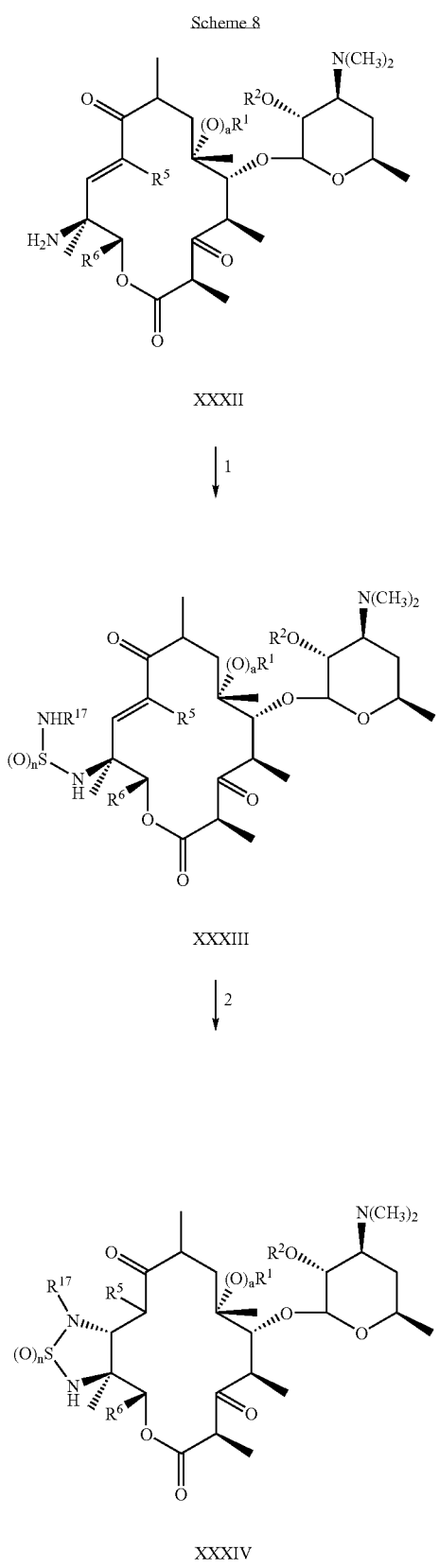
Scheme 8
XXXII
XXXIII
XXXIV
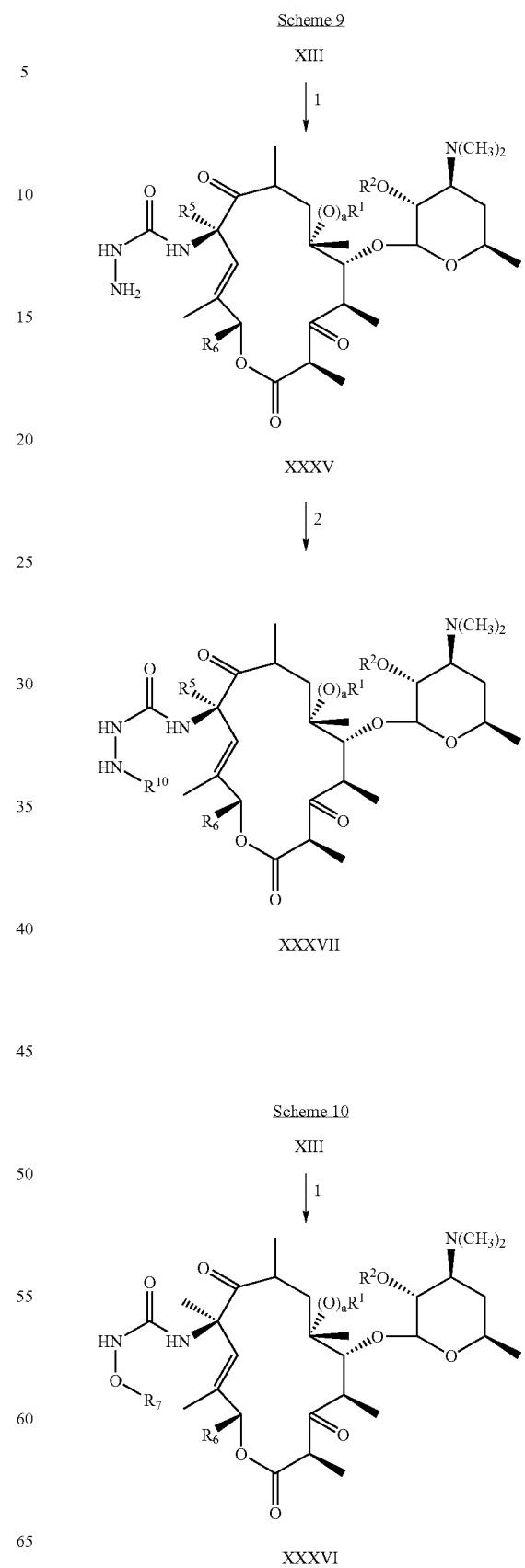
Scheme 9
XIII
XXXV
XXXVII
Scheme 10
XIII
XXXVI Scheme 11

XXVII

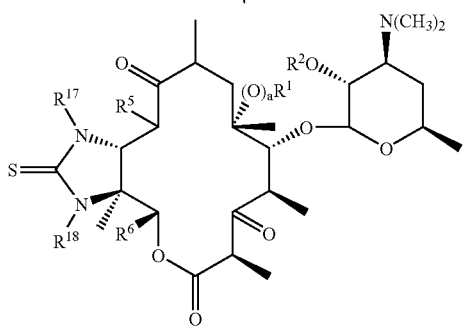

XXVIII

Scheme 12

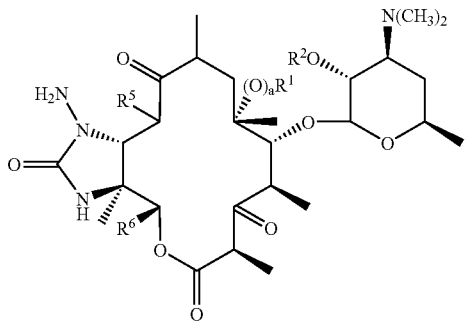

XXIX

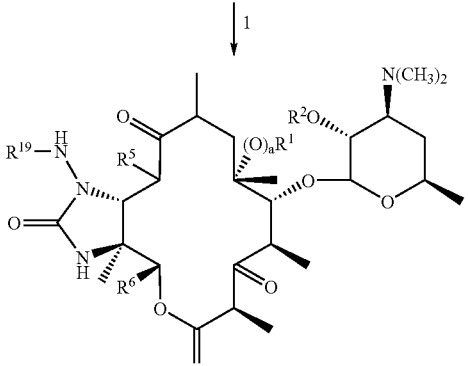

XXXX

In reaction 1 of Preparation A, the compound of formula VII, wherein $R^{22}$ is a good leaving group, such as ($C_1$–$C_6$) alkylsulfonyloxy, ($C_6$–$C_{10}$)arylsulfonyloxy, ($C_1$–$C_6$)acyloxy or imidizolylcarbonyloxy, is converted to the corresponding ketene acetal compound of formula VI by treating VII with a base, such as 1,8-diazabicyclo[5.4.0]undec-7-ene, 1,5-diazabicyclo[4.3.0]non-5-ene, ethyldiisopropylamine, triethylamine, lithium hexamethyldisilazide or potassium hexamethyldisilazide, preferably 1,8-diazabicyclo[5.4.0]undec-7-ene, in the presence of a polar apotic solvent, such as acetonitrile, dimethylformamide, tetrahydrofuran, preferably acetonitrile. The reaction is stirred at a temperature between about 20° C. to about 100° C., preferably about 80° C., for a time period between about 0.5 hours to about 6 hours, preferably about 2 hours.

In reaction 2 of Preparation A, the ketene acetal compound of formula VI is converted to the corresponding azide compound of formula V by reacting VI with an azidonation reagent, such as azidotrimethylsilane, sodium azide or tributyltin azide, preferably azidotrimethylsilane, in the presence of a Lewis acid, such as tin(IV)chloride, titanium(IV)chloride, boron trifluoride diethyl etherate or aluminum trichloride, preferably tin(IV)chloride, and an aprotic solvent. Suitable solvents include dichloromethane, dichloroethane, chloroform or carbontetrachloride, preferably dichloromethane. The reaction is carried out at a temperature between about −78° C. to about 25° C., preferably about 0° C., for a time period between about 3 hours to about 12 hours, preferably about 6 hours.

In reaction 3 of Preparation A, the azide compound of formula V is converted to the corresponding amino compound of formula IV by reducing V in the presence of hydrogen, a catalyst, such as palladium on carbon, palladium on calcium carbonate, platinum(IV)oxide or ruthenium on carbon, preferably palladium on calcium carbonate, and a solvent, such as ethanol, methanol or ethyl acetate, preferably ethanol. The reaction is carried out under a pressure of about 1 psi to about 50 psi, preferably about 20 psi, at a temperature between about 0° C. to about 50° C., preferably about 25° C., for a time period between 1 hours to about 6 hours, preferably about 2.5 hours.

In reaction 4 of Preparation A, the amino compound of formula IV is converted to the corresponding isocyanate compound of formula XXII by reacting IV with phosgene or triphosgene in the presence of a base, such as triethylamine or pyridine, and an aprotic solvent, such as tetrahydrofuran or dioxane. The reaction is carried out at a temperature between about 0° C. to about 50° C., preferably about 0° C., for a time period between 0.5 hours to about 12 hours, preferably about 2 hours.

In reaction 5 of Preparation A, the compound of formula V is converted to the corresponding compound of formula IX by heating V to a temperature between about 30° C. to about 100° C., preferably about 70° C., in ethanol, tetrahydrofuran, or dioxane for a time period between about 0.5 hours to about 6 hours, preferably about 2 hours.

In reaction 6 of Preparation A, the azide compound of formula IX is converted to the corresponding amino compound of formula VIII according to the procedure described above in reaction 3 of Preparation A.

In reaction 1 of Preparation B, the amino compound of formula VIII is converted to the corresponding isocyanate compound of formula XIII according to the procedure described above in reaction 4 of Scheme A.

In reaction 1 of Preparation C, the ketene acetal compound of formula VI is converted to the corresponding compound of formula XXXIX, when $R^4$ is methylene substituted by one to two nitro, $R^{14}O_2C$ or cyano groups, by reacting VI with a compound of the formula, $R^4H$, in the presence of a base, such as 1,8-diazabicyclo[5.4.0]undec-7-ene, 1,5-diazabicyclo[4.3.0]non-5-ene, triethylamine, sodium hydride or lithium bis(trimethylsilyl)amide, preferably as 1,8-diazabicyclo[5.4.0]undec-7-ene, and an aprotic solvent, such as tetrahydrofuran, acetonitrile or dimethylformamide, preferably acetonitrile. The reaction is carried out at a temperature between about −20° C. to about 100° C., preferably about 80° C., for a time period between about 0.5 hours to about 6 hours, preferably about 2 hours.

In reaction 1 of Scheme 1, the amino compound of formula IV is converted to the corresponding amide compound of formula X by reacting IV with a compound of the formula, $R^{10}$—CO—X, wherein X is chloro, bromo or an anhydride, in the presence of a base, such as pyridine or triethylamine. Suitable solvents include dichlormethane, dichloroethane, tetrahydrofuran or dioxane, preferably tetrahydrofuran. The reaction is stirred at a temperature between about 0° C. to about 50° C., preferably about 0° C., for a time period between about 1 hours to about 24 hours, preferably about 12 hours. The amide formation of the compound of formula X can also be effected by reacting IV with the carboxylic acid compound of the formula, $R^{10}$—COOH, in the presence of a dehydrating agent, such as 1,3-dicyclohexylcarbodiimide or 1-(3-dimethylaminopropyl)-3-ethylcarbodiimide.

In reaction 2 of Scheme 1, the amino compound of formula IV is converted to the corresponding urea compound of formula XI by reacting IV with phosgene or triphosgene in the presence of a base, such as triethylamine or pyridine, and an aprotic solvent, such as tetrahydrofuran or dioxane. An amine of the formula, $R^{10}NH_2$, is added to the reaction mixture so formed in the presence of tetrahydrofuran, dioxane or dimethylformamide. The reaction is carried out at a temperature between about 0° C. to about 100° C., preferably about 65° C., for a time period between about 0.5 hours to about 12 hours, preferably about 6 hours. The urea formulation of the compound of formula XI can also be effected by reacting IV with a compound of the formula, $R^{10}N=C=O$, in the presence of an aprotic solvent, such as tetrahydrofuran, dioxane or dimethylformamide. The reaction is carried out at a temperature between about 0° C. to about 50° C., preferably about 25° C., for a time period between about 0.5 hours to about 24 hours, preferably about 12 hours.

In reaction 3 of Scheme 1, the amino compound of formula IV is converted to the corresponding carbamate compound of formula XII by reacting IV with a chloroformate of the formula, $R^{10}COCl$, in the presence of a base, such as triethylamine, pyridine or ethyldiisopropylamine, and an aprotic solvent. Suitable solvents include tetrahydrofuran, dioxane or dimethylformamide. The reaction is carried out at a temperature between about 0° C. to about 50° C., preferably about 25° C., for a time period between about 0.5 hours to about 24 hours, preferably about 6 hours. The compound of formula XII can also be prepared by reacting the compound of the formula XXII with an alcohol of the formula $R^{10}OH$.

In reaction 4 of Scheme 1, the amino compound of formula IV is converted to the corresponding compound of formula XIII by the reductive amination of IV by use of an aldehyde of the formula, $R^{10}CHO$, or ketone, and a reducing agent, such as sodium cyanoborohydride, sodium triacetoxyborohydride or hydrogen in the presence of a catalyst, such as palladium on carbon. Suitable solvents include ethanol or methanol. The reaction mixture is stirred at a temperature between about 0° C. to about 50° C., preferably about 25° C., for a time period between about 0.5 hours to about 24 hours, preferably about 12 hours.

In reaction 1 of Scheme 2, the ketene acetal compound of formula VI is converted to the corresponding compound of formula XIV by reacting VI with an alcohol compound of the formula, $R^{10}$—OH, in the presence of an acid, such as tin(IV)chloride, titanium(IV)chloride, titanium(IV)isopropoxide or boron trifluoride diethyl etherate, and an aprotic solvent, such as methylene chloride and dichloroethane. The reaction is carried out at a temperature between about −78° C. to room temperature, preferably about 0° C., for a time period between about 1 hour to about 24 hours preferably about 6 hours.

In reaction 2 of Scheme 2, the ketene acetal compound of formula VI is converted to the corresponding compound of formula XV by reacting VI with a thiol compound of the formula, $R^{10}$—SH, in the presence of an acid, such as tin(IV)chloride, titanium(IV)chloride, titanium(IV)isopropoxide or boron trifluoride diethyl etherate, and a polar aprotic solvent, such as methylene chloride. The reaction is carried out at a temperature between about −78° C. to room temperature, preferably about 0° C., for a time period between about 1 hour to about 24 hours, preferably about 6 hours.

In reaction 3 of Scheme 2, the ketene acetal compound of formula VI is converted to the corresponding cyano compound of formula XVI by reacting VI with trimethylsilyl cyanide or tetrabutylammonium cyanide in the presence of an acid, such as tin(IV)chloride, and an aprotic solvent such as dichloromethane and dichloroethane. The reaction is carried out at a temperature between about −78° C. to room temperature, preferably about 0° C., for a time period between about 1 hour to about 24 hours, preferably about 6 hours.

In reaction 4 of Scheme 2, the ketene acetal compound of formula VI is converted to the corresponding compound of formula XVII by reacting VI with trimethylsilyl isothiocyanate in the presence of an acid, such as tin(IV)chloride, and an aprotic solvent, such as methylene chloride, dichloroethane tetrahydrofuran or dioxane for a time period between about 1 hour to about 24 hours, preferably about 6 hours. An amine of the formula, $R^{10}NH_2$, is added to the reaction mixture so formed in the presence of tetrahydrofuran, dioxane or dimethylformamide. The reaction is carried out at a temperature between about 0° C. to about 50° C., preferably about 25° C., for a time period between about 0.5 hours to about 24 hours, preferably about 6 hours.

In reaction 1 of Scheme 3, the amino compound of formula VIII is converted to the corresponding amide compound of formula XVIII according to the procedure described above in reaction 1 of Scheme 1.

In reaction 2 of Scheme 3, the amino compound of formula VIII is converted to the corresponding urea compound of formula XIX according to the procedure described above in reaction 2 of Scheme 1.

In reaction 3 of Scheme 3, the amino compound of formula VIII is converted to the corresponding carbamate compound of formula XX according to the procedure described above in reaction 3 of Scheme 1.

In reaction 4 of Scheme 3, the amino compound of formula VIII is converted to the corresponding compound of formula XXI according to the procedure described above in reaction 4 of Scheme 1.

In reaction 1 of Scheme 4, the isocyanate compound of formula XXII is converted to the corresponding compound of formula XXIII by reacting XXII with a compound of the formula, $R^{19}ONH_2$, in the presence of an aprotic solvent, such as tetrahydrofuran, dioxane or dimethylformamide. The reaction is carried out at a temperature between about 0° C. to about 100° C., preferably about 25° C., for a time period between about 0.5 hours to about 12 hours, preferably about 6 hours.

In reaction 2 of Scheme 4, the compound of formula XXIII is converted to the corresponding cyclic urea compound of formula XIV by heating XXIII in the presence or absence of potassium hydroxide, sodium hydroxide, potassium tert-butoxide or acetic acid and a solvent, such as toluene, benzene or dimethylformamide. The reaction is carried out at a temperature between about 25° C. to about 100° C., preferably about 80° C., for a time period between 0.5 hours to about 12 hours, preferably about 3 hours.

In reaction 1 of Scheme 5, the urea compound of formula XI is converted to the corresponding cyclic urea compound of formula XXV according to the procedure described above in reaction 2 of Scheme 4.

In reaction 1 of Scheme 6, the ketene acetal compound of formula IV is converted to the corresponding thioisocyanate compound of formula XXVI by reacting IV with trimethylsilyl isothiocyanate in the presence of a Lewis acid, such as tin(IV)chloride, titanium(IV)chloride, boron trifloride diethyl etherate or aluminum trichloride, preferably tin(IV) chloride, and an aprotic solvent. Suitable solvents include ichloromethane, dichloroethane, chloroform or carbontetrachloride, preferably dichloromethane. The reaction is carried out at a temperature between about −78° C. to about 50° C., preferably about 0° C., for a time period between about 0.5 hours to about 24 hours, preferably about 12 hours.

In reaction 2 of Scheme 6, the thioisocyanate of formula XXVI is converted to the corresponding thiourea compound of formula XXVII according to the procedure described above in reaction 2 of Scheme 1.

In reaction 2 of Scheme 6, the thiourea compound of formula XXVII is converted to the corresponding aminothiazoline compound of formula XXVIII according to the procedure described above in reaction 2 of Scheme 4.

In reaction 1 of Scheme 7, the cyclic urea compound of formula XXIX is converted to the corresponding compound of formula XXX by reacting XXIX with a compound of the formula, NHOR$^{16}$, in the presence of ethanol or pyridine. The reaction is carried out at a temperature between about 25° C. to about 100° C., preferably about 80° C., for a time period between about 1 hour to about 48 hours, preferably about 24 hours.

In reaction 2 of Scheme 7, the compound of reaction XXX is converted to the corresponding compound of formula XXXI by reacting XXX with an aldehyde compound of the formula, R$^{19}$CHO, in the presence of sodium borohydride and a polar aprotic solvent, such as methanol or ethanol, preferably methanol. The reaction is carried out at a temperature between about 0° C. to about 50° C., preferably about 25° C., for a time period between about 0.5 hours to about 24 hours, preferably about 12 hours.

In reaction 1 of Scheme 8, the amino compound of formula XXXII is converted to the corresponding compound of formula XXXIII by reacting XXXII with sulfonyl diimidazole, sulfuryl chloride or thionyl chloride in the presence of a base, such as triethylamine or pyridine and an aprotic solvent, such as tetrahydrofuran, dioxane or methylene chloride. The reaction is carried out at a temperature between about −78° C. to about 25° C., preferably about 0° C., for a time period between about 0.5 hours to about 24 hours, preferably about 12 hours. An amine of the formula, R$^{17}$NH$_2$, is added to the reaction mixture so formed in the presence of a base, such as triethylamine or pyridine and an aprotic solvent, such as tetrahydrofuran, dioxane or methylene chloride. The reaction is carried out at a temperature between about 0° C. to about 25° C., preferably about 0° C., for a time period between about 0.5 hours to about 24 hours, preferably about 6 hours.

In reaction 2 of Scheme 8, the compound of formula XXXIII is converted the corresponding to the compound of formula XXXIV by heating XXXIII in tetrahydrofuran or dimethylformamide in the presence or absence of potassium tert-butoxide or acetic acid. The reaction is carried out at a temperature between about 60° C. to about 100° C., preferably about 85° C., for a time period between about 0.5 hours to about 12 hours, preferably about 2 hours.

In reaction 1 of Scheme 9, the compound of formula XIII is converted to the corresponding compound of formula XXXV according to the procedure described above in reaction 1 of Scheme 4.

In reaction 2 of Scheme 9, the compound of formula XXXV is converted to the corresponding compound of formula XXXVII by reacting XXXV with an aldehyde of the formula, R$^{10}$CHO, and a reducing agent, such as sodium cyanoborohydride. Suitable solvents include methanol, ethanol or dichloroethane. The reaction mixture is stirred at a temperature between about 0° C. to about 50° C., preferably about 25° C., for a time period between about 0.5 hours to about 24 hours, preferably about 12 hours.

In reaction 1 of Scheme 10, the isocyanate compound of formula XIII is converted to the corresponding compound of formula XXXVI according to the procedure described above in reaction 1 of Scheme 4.

In reaction 1 of Scheme 11, the thiourea compound of formula XXVII is converted to the corresponding cyclic thiourea compound of formula XXXVIII according to the procedure described above in reaction 2 of Scheme 4.

In reaction 1 of Scheme 12, the compound of formula XXIX is converted to the corresponding compound of formula XXXX according to the procedure described above in reaction 2 of Scheme 9.

The starting compound of formula VII can be prepared as described in U.S. Pat. No. 5,543,400. The starting compounds of formula VII where R$^1$ is various groups can be prepared as described in WO 98/09978.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The activity of the compounds of the present invention against bacterial and protozoa pathogens is demonstrated by the compound's ability to inhibit growth of defined strains of human (Assay I) or animal (Assays II and III) pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562–2566 (1996). The assay is performed in microtiter trays and interpreted according to *Performance Standards for Antimicrobial Disk Susceptibility Tests—Sixth Edition; Approved Standard*, published by The National Committee for Clinical Laboratory Standards (NCCLS) guidelines; the minimum inhibitory concentration (MIC) is used to compare strains. Compounds are initially dissolved in dimethylsulfoxide (DMSO) as 40 mg/ml stock solutions.

| Strain Designation | Macrolide Resistance Mechanism(s) |
|---|---|
| *Staphylococcus aureus* 1116 | susceptible parent |
| *Staphylococcus aureus* 1117 | ermB |
| *Staphylococcus aureus* 0052 | susceptible parent |
| *Staphylococcus aureus* 1120 | ermC |
| *Staphylococcus aureus* 1032 | msrA, mph, esterase |
| *Staphylococcus hemolyticus* 1006 | msrA, mph |
| *Streptococcus pyogenes* 0203 | susceptible parent |
| *Streptococcus pyogenes* 1079 | ermB |
| *Streptococcus pyogenes* 1062 | susceptible parent |
| *Streptococcus pyogenes* 1061 | ermB |
| *Streptococcus pyogenes* 1064 | ermB |
| *Streptococcus agalactiae* 1024 | susceptible parent |
| *Streptococcus agalactiae* 1023 | ermB |
| *Streptococcus pneumoniae* 1016 | susceptible |
| *Streptococcus pneumoniae* 1046 | ermB |
| *Streptococcus pneumoniae* 1095 | ermB |
| *Streptococcus pneumoniae* 1175 | mefE |
| *Streptococcus pneumoniae* 0085 | susceptible |
| *Haemophilus influenzae* 0131 | susceptible |
| *Moraxella catarrhalis* 0040 | susceptible |
| *Moraxella catarrhalis* 1055 | erythromycin intermediate resistance |
| *Escherichia coli* 0266 | susceptible |

Assay II is utilized to test for activity against *Pasteurella multocida* and Assay III is utilized to test for activity against *Pasteurella haemolytica*.

Assay II

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 μl of dimethylsulfoxide (DMSO). Dilutions of the test compound are prepared using uninoculated BHI broth. The concentrations of the test compound used range from 200 μg/ml to 0.098 μg/ml by two-fold serial dilutions. The *P. multocida* inoculated BHI is diluted with uninoculated BHI broth to make a $10^4$ cell suspension per 200 μl. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 μl of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 μl of the *P. haemolytica* culture is inoculated onto BHI agar plates containing the various concentrations of the test compound using a Steers Replicator and incubated for 18 hours at 37° C. Initial concentrations of the test compound range from 100–200 μg/ml. The MIC is equal to the concentration of the test compound exhibiting 100% inhibition of growth of *P. haemotica* as determined by comparison with an uninoculated control.

The in vivo activity of the compounds of formula (I) can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a $3\times10^3$ CFU/ml bacterial suspension (*P. multocida* strain 59A006) intraperitoneally. Each experiment has at least 3 non-medicated control groups including one infected with 0.1× challenge dose and two infected with 1× challenge dose; a 10× challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The *P. multocida* model monitoring continues for 96 hours (four days) post challenge.

The $PD_{50}$ is a calculated dose at which the compound tested protects 50% of a group of mice from mortality due to the bacterial infection which would be lethal in the absence of drug treatment.

The compounds of formula I, and the pharmaceutically acceptable salts thereof (hereinafter "the active compounds"), may be adminstered through oral, parenteral, topical, or rectal routes in the treatment or prevention of bacterial or protozoa infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral adinistration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be adminstered in the form of liposome delivery systems, such as small unilameilar vesicles, large unilameilar vesicles and multilameilar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoylresidues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The Examples provided below illustrate specific embodiments of the invention, but the invention is not limited in scope to the Examples specifically exemplified.

EXAMPLE 1

Formula XIII (a is 1; $R^1$ is methyl; $R^2$ is acetyl; C-8 methyl is α or β; $R^4$ is nitromethyl and $R^6$ is ethyl)

1,8-Diazabicyclo[5.4.0]undec-7-ene (76 µl, 0.5 mmol) was added to a solution of formula VII (a is 1; $R^1$ is methyl; $R^2$ is acetyl; C-8 methyl is α; $R^3$ is imidazolecarbonyl; $R^4$ is hydrogen and $R^6$ is ethyl) (71 mg, 0.1 mmol and nitromethane (76 µl, 0.5 mmol) in 2 mL of acetonitrile.

The resulting solution was refluxed for 1.5 hours under nitrogen. Ethyl acetate (10 mL) was added to the reaction mixture and the organic layer was washed with saturated sodium dihydrogen phosphate solution.

The ethyl acetate solution was washed with brine and dried over $Na_2SO_4$. The residue obtained after evaportion of the solvent was chromatoraphed on silica gel (TLC, 5% MeOH—0.5% $NH_4OH$—$CH_2Cl_2$) to give 19 mg (29%) of the titled compound (C-8 methyl α); MS m/e 655 (M+1) and 11 mg (17%) of the titled compound (C-8 methyl β); MS m/e 655 (M+1).

EXAMPLE 2

Formula VI (a is 1; $R^1$ is methyl; $R^2$ is acetyl; C-8 methyl is α or β; and $R^6$ is ethyl)

1,8-Diazabicyclo[5.4.0]undec-7-ene (90 µl, 0.61 mmol) was added to a solution of VII (a is 1; $R^1$ is methyl; $R^2$ is acetyl; C-8 methyl is a; $R^3$ is imidazolecarbonyl; $R^4$ is hydrogen and $R^6$ is ethyl) (4.30 grams, 6.1 mmol) in 120 mL of dry acetonitrile.

The solution was refluxed for 4 hours. The solvent was evaporated and the residue was chromatographed on silica gel (1% methanol—0.5% triethylamine-Methyl t-butyl ether) to give 2.44 grams (67%) of the titled compound (C-8 methyl α) and 643 mg (18%) of the titled compound (C-8 methyl β); MS m/e 594 (M+1).

EXAMPLE 3

Formula V (a is 1; $R^1$ is methyl; $R^2$ is acetyl; C-8 methyl is α; and $R^6$ is ethyl)

A compound of formula VI (a is 1; $R^1$ is methyl; $R^2$ is acetyl; C-8 methyl is α; and $R^6$ is ethyl) (555 mg, 0.94 mmole) was dissolved 40 mL of ethylene and cooled to −78°. Trimethylsilyl azide (744 µL of 1M tin(IV)chloride solution in methylene chloride) was added dropwise. The reaction mixture was slowly warmed to room temperature and stirred overnight. The reaction was quenched by addition of satrated sodium hydrogen carbonate solution, and the product was extracted with methylene chloride. The methylene chloride layer was washed with brine and dried over sodium sulfate. The solvent was evaporated and the residue was chromatographed to give 410 mg (69%) of the titled compound; MS m/e 637 (M+1).

EXAMPLE 4

Formula X (a is 1; $R^1$ is methyl; $R^2$ is acetyl; C-8 methyl is α; $R^6$ is ethyl and $R^7$ is methyl) and Formula XVIII (a is 1; $R^1$ is methyl; $R^2$ is acetyl; C-8 methyl is α; $R^6$ is ethyl and $R^7$ is methyl)

Lindlar catalyst (25 mg) was added to a solution of a compound of formula V (a is 1; $R^1$ is methyl; $R^2$ is acetyl; C-8 methyl is α; and $R^6$ is ethyl) (25 mg, 0.039 mmol) in 5 mL of ethanol, and the resulting solution was hydrogenated in a Parr shaker with 20 psi of hydrogen at room temperature for 2 hours. The solution was filtered through celite and the solvent was evaporated. The residue was dissolved in 2 mL of tetrahydrofuran and treate with 50 µL of pyridine and 50 µL acetic anhydride at 4° C. overnight. The solvent and exess reagents were evaporated and the residue was chromatographed on silica gel plates (5% methanol—0.5% $NH_4OH$—$CH_2Cl_2$) to give 6.6 mg (26%) of formula X; m/e 653 (M+1) and 2.7 mg (11%) of formula XVIII; MS m/e 653 (M+1).

EXAMPLE 5

Formula XXIX (a is 1; $R^1$ is methyl; $R^2$ is acetyl; C-8 methyl is α; $R^5$ is α-methyl and $R^6$ is ethyl) and Formula XXXV (a is 1; $R^1$ is methyl; $R^2$ is acetyl; C-8 methyl is α; and $R^6$ is ethyl)

Lindlar catalyst (137 mg) was added to a solution of a compound or formula V (a is 1; $R^1$ is methyl; $R^2$ is acetyl; C-8 methyl is α; and $R^6$ is ethyl) (137 mg, 0.215 mmol) in 15 mL of ethanol. The resulting solution was hydrogenated at 20 psi of hydrogen for 2 hours. The solution was filtered through celite and the solvent was removed under reduced ressure. The residue was dissolved in 5 mL of tetrahydrofuran and cooled in an ice-bath. Triethylamine (85 µL 0.611 mmol, 2.84 eq) and phosgene (0.25 mL of 1.93 M solution in toluene, 0.483 mmol, 2.24 eq) were added. The solution was stirred at 0° for 2 hours. The reaction mixture was diluted with 25 mL of ethyl acetate and washed with a saturated sodium hydrogen carbonate solution and brine.

After drying over sodium sulfate, the solvent was removed under reduced pressure. The residue was then dissolved in 2 mL of dimethylformamide and anhydrous hydrazine (67 µL, 2.15 mmol, 10 eq) was added. The resulting solution was heated at 60° C. for 6 hours. Dimethylformamide was removed under reduced pressure and the residue was chromatographed on $SiO_2$ (5% methanol—0.5% $NH_4OH$—$CH_2Cl_2$) to give two mjor fractions. The first fraction was further chromatographed on $SiO_2$ plates (7.5% MeOH—0.75% $NH_4OH$—$CH_2Cl_2$) to give 9 mg (7%) of formula XXIX; Ms m/e 627 (M+1).

The second fraction was further chromatographed on $SiO_2$ plates (5% MeOH—5% triethylaminemethyl tert-butyl ether) to give 12 mg (9%) of formula XXXV; MS m/e 627.

EXAMPLE 6

Formula L (a is 1; $R^1$ is methyl, $R^2$ is acetyl, C-8 methyl is α; $R^5$ is α-methyl and $R^6$ is ethyl)

A compound of formula XXIX (a is 1; $R^1$ is methyl; $R^2$ is acetyl; C-8 methyl is α; $R^5$ is methyl and $R^6$ is ethyl) (12 m, 0.027 mmol) and 3-(quinolin-4-yl)propionaldehyde (10 mg, 0.054 mmol) in 1 mL of toluene were heated to 90° for 14 hours. Toluene was removed under reduced pressure, and the residue was dissolved in 1 mL of methanol (MeOH). Sodium cyanoborohydride (16.9 mg, 0.27 mol) and acetic acid (25 μL, 0.43 mmol) were added, and the resulting solution was stirred at room temperature for 46 hours. The solvent was removed and the residue was dissolved in methylene chloride and washed with a saturated sodium hydrogen carbonate solution and brine. After drying over sodium sulfate, the solvent was evaporated and the residue was chromatographed on silica gel (TLC, 5% methanol—0.5% $NH_4OH$-methylene chloride) to give 13 mg of slightly yellow glass. This material was further chromatographed on silica gel (TLC, 5% MeOH—5%-triethylamine-methyl t-butyl ether) to give 10 mg (47%) of the titled compound; MS m/e 839 (M+1).

EXAMPLE 7

Formula XI (a is 1; $R^1$ is methyl; $R^2$ is acetyl; C-8 methyl is α; $R^6$ is ethyl and $R^7$ is 4-(3-pyridinyl)-1H-imidazol-1-butyl) and Formula XIX (a is 1; $R^1$ is methyl; $R^2$ is acetyl; C-8 methyl is α; $R^6$ is ethyl and $R^7$ is 4-(3-pyridinyl)-1H-imidazol-1-butyl)

Lindlar catalyst (137 mg) was added to a solution of a compound of formula V (a is 1; $R^1$ is methyl; $R^2$ is acetyl; C-8 methyl is α; and $R^6$ is ethyl) (137 mg, 0.215 mmol) in 15 mL of ethanol. The resulting solution was hydrogenated at 20 psi of hydrogen for 2 hours. The solution was filtered through celite and the solvent was removed under reduced pressure. The residue was dissolved in 5 mL of THF and cooled in an ice-bath. Triethylamine (85 μL, 0.611 mmol, 2.84 eq) and a phosgene solution in toluene (250 μL of 1.93 M solution, 0.483 mmol, 2.24 eq) was added. The solution was stirred at 0° for 2 hours. The reaction mixture was diluted with 25 mL of ethyl acetate and washed with a saturated $NaHCO_3$ solution and brine. After drying over $Na_2SO_4$, the solvent was removed under reduced pressure. The residue was dissolved in 2 mL of DMF and 4-(3-pyridinyl)-1H-imidazol-1-butylamine (139 mg, 0.645 mmol) was added.

The solution was warmed to 60° C. for 6 hours. DMF was removed under reduced pressure, and the residue was chromatographed on silica gel (TLC 5%—MeOH—0.5% $NH_4OH$—$CHCl_2$) to give two fractions. The less polar fraction was further chromatographed on preparative $SiO_2$ TLC (7.5% MeOH—0.75% $NH_4OH$—$CH_2Cl_2$) to give 5 mg (3%) of a compound of formula XI: MS m/e 853 (M+1).

The more polar fraction was further chromatographed on silica gel (TLC 5% MeOH—5% trethylamine-methyl t-butyl ether) to give 12 mg (7%) of a compound of formula XIX: MS m/e 853 (M+1).

EXAMPLE 7B

Formula XXV (a is 1; $R^1$ is methyl; $R^2$ is acetyl, C-8 methyl is α; $R^6$ is ethyl; and $R^7$ is 4-(3-pyridyl)1H-imidazol-1-butyl)

A solution of XI (a is 1; $R^1$ is methyl; $R^2$ is acetyl; C-8 methyl is α; $R^6$ is ethyl; and $R^7$ is 4-(3-pyridinyl)1H-imidazol-1-butyl) (35 mg, 0.041 mmol) and 3.5 mg of potassium hydroxide in 1 ml of toluene was heated at 90° C. for 1 hour. The cooled solution was diluted with ethyl acetate and washed with water. The aqueous layer was extracted with fresh ethyl acetate. The combined orgaic layers were dried over $Na_2SO_4$, and evaporated. The residue was chromatographed on silica gel (TLC 10% MeOH—$CH_2Cl_2$) to give 15 mg (43%) of the title compound: MS m/e 853.

EXAMPLE 8

Formula XI (a is 1; $R^1$ is methyl; $R^2$ is hydrogen; C-8 methyl is α; $R^6$ is Ethyl and $R^{10}$ is 4-4(3-pyridinyl)-1H-imidazol-1-butyl)

A compound of formula XI (a is 1; $R^1$ is methyl; $R^2$ is acetyl; C-8 methyl is a; $R^6$ is ethyl and $R^7$ is 4-(3-pyridinyl)1H-imidazol-1-butyl) (6 mg, 7 mmol) was warmed in methanol for 1 hour. Methanol was then evaporated and the residue was chromatographed on silica gel (TLC 10% MeOH—1% $NH_4OH$—$CH_2Cl_2$) to give 4 mg (70%) of the titled compound: MS m/e 812 (M+1).

EXAMPLE 9

Formula XXVI (a is 1; $R^1$ is methyl; $R^2$ is acetyl; C-8 methyl is α or β; $R^5$ is methyl and $R^6$ is ethyl)

Formula VI (a is 1; $R^1$ is methyl; $R^2$ is acetyl; C-8 methyl is α or β; and $R^6$ is ethyl) (54 mg, 0.091 mmol) was dissolved in 5 mL of $CH_2Cl_2$ and cooled in a dry ice-acetone bath. Trimethylsilyl isothiocyanate (128 μL, 0.91 mmol) and a tin(IV)chloride solution (137 μL of 1M solution in methylene chloride were added and the resulting solution was gradually warmed up to room temperature overnight. A saturated sodium hydrogen carbonate solution was then added and the products were extracted with ethyl acetate. The organic layer was washed with brine and dried over sodium sulfate. The residue obtained after evaporation of the solvents were chromatographed on silica gel (hexane:acetone=2:1) to give 10 mg (17%) of the titled compound: MS m/e 653.

EXAMPLE 10

Formula XIV (a is 1; $R^1$ is methyl; $R^2$ is acetyl; C-8 methyl is α; $R^6$ is ethyl and $R^7$ is propagyl)

A compound of formula VI (a is 1; $R^1$ is methyl; $R^2$ is acetyl; C-8 methyl is α or β; and $R^6$ is ethyl)(118 mg, 0.2 mmol) was dissolved in 10 mL of dry methylene chloride and cooled to −78°. Propagyl alcohol (35 μL, 0.6 mmol) and a 1M tin(IV)chloride solution in methylene chloride (220 μL, 0.22 mmol) were added and the solution was gradually warmed to room temperature overnight. The reaction was quenched by addition of saturated sodium hydrogen carbonate solution and the methylene chloride solution was washed with brine and dried over sodium sulfate. The residue obtained after evaporation of methylene chloride was chromatographed on silica gel (TLC 5% methanol—2.5% triethylamin-methyl t-butyl ether). The appropriate band was extracted with 5% methanol—methylene chloride and rechromatographed (10% acetone-hexane) to give 6 mg (5%) of the titled compound MS m/e 649 (M+1).

The invention claimed is:

1. A compound of the formula

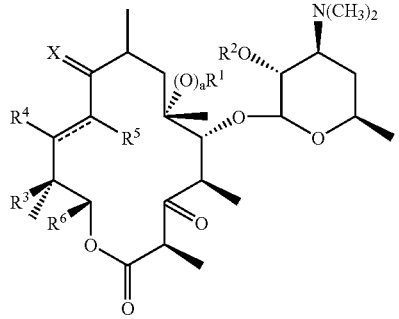

I or the pharmaceutically acceptable salt thereof; wherein the dashed line between positions 10 and 11 represents an optional double bond;

a is 0 or 1;

$R^1$ is hydrogen or $(C_1-C_{10})$alkyl optionally substituted by fluoro, cyano, $R^7$, $R^7$ $O_2$ C, $R^7$ C(O)NH or $R^7$ S(O)$_n$ wherein n is 0, 1 or 2 and $R^7$ is $(C_1-C_6)$alkyl, $(C_2-C_{12})$alkenyl, $(C_2-C_{12})$alkynyl, $(C_3-C_{10})$cycloalkyl$(C_1-C_6)$alkyl, $(C_2-C_9)$heterocycloalkyl$(C_1-C_6)$ alkyl, $(C_6-C_{10})$aryl$(C_1-C_6)$alkyl or $(C_2-C_9)$heteroaryl$(C_1-C_6)$alkyl wherein the alkyl, alkenyl, alkynyl, cycloalkyl, heterocycloalkyl, aryl and heteroaryl groups are optionally substituted by one to three of halo, $(C_1-C_3)$alkoxy, hydroxy, nitro, cyano, $(C_6-C_{10})$aryl, $(C_2-C_9)$heteroaryl, $R^8R^9N$, $R^8C(O)$, $R^8C(O)O$, $R^8OC(O)$, $R^8C(O)NH$, $R^8NHC(O)$, $R^8R^9NC(O)$ or $R^8OC(O)_2$ wherein $R^8$ and $R^9$ are each independently hydrogen, $(C_1-C_6)$alkyl optionally substituted by $(C_6-C_{10})$aryl or $(C_2-C_9)$heteroaryl;

$R^2$ is hydrogen or a hydroxy protecting group;

$R^3$ is amino, cyano, $N_3$, $R^{10}NH$, $R^{10}C(O)NH$, $R^{10}NHC(O)NH$, $R^{10}NHC(S)NH$, $R^{10}NHNHC(O)NH$, $R^{10}ONHC(O)NH$, $R^{10}$ O, $R^{10}$ OC(O)NH, $R^{10}$ S(O)$_n$, $R^{10}$phosphoramido, $R^{10}$sulfonamido, SH, or $R^{10}S$ wherein n is defined above and $R^{10}$ is $(C_1-C_6)$alkyl, $(C_2-C_{12})$alkenyl, $(C_2-C_{12})$alkynyl, $(C_3-C_{10})$cycloalkyl$(C_1-C_6)$alkyl, $(C_2-C_9)$heterocycloalkyl$(C_1-C_6)$alkyl, $(C_6-C_{10})$aryl, $(C_6-C_{10})$aryl$(C_1-C_6)$alkyl or $(C_2-C_9)$heteroaryl$(C_1-C_6)$alkyl; wherein the alkyl, alkenyl, alkynyl, cycloalkyl, heterocycloalkyl, aryl and heteroaryl groups are optionally substituted by one to three substituents independently selected from halo, $(C_1-C_3)$alkoxy, hydroxy, nitro, cyano, $(C_6-C_{10})$aryl, $(C_2-C_9)$heteroaryl, $R^8R^9N$, $R^8C(O)$, $R^8C(O)O$, $R^8OC(O)$, $R^8C(O)NH$, $R^8NHC(O)$, $R^8R^9NC(O)$ or $R8OC(O)_2$ wherein $R^8$ and $R^9$ are each independently hydrogen, $(C_1-C_6)$alkyl optionally substituted by $(C_6-C_{10})$aryl or $(C_2-C_9)$heteroaryl; or $R^3$ is $R^{12}R^{13}N$ wherein $R^{12}$ and $R^{13}$ are each independently hydrogen, $(C_1-C_6)$alkyl, $(C_6-C_{10})$aryl$(C_1-C_6)$alkyl or $(C_2-C_9)$heteroaryl$(C_1-C_6)$alkyl;

$R^4$ is hydrogen, or is methyl optionally substituted by one to of two nitro, cyano, $R^{14}C(O)$ or $R^{14}OC(O)$; or $R^4$ is $N_3$, $R^{14}$ O, $R^{14}$ NH, $R^{14}$ S wherein $R^{14}$ is $(C_1-C_6)$alkyl, $(C_2-C_{12})$alkenyl, $(C_2-C_{12})$alkynyl, $(C_3-C_{10})$cycloalkyl$(C_1-C_6)$alkyl, $(C_2-C_9)$heterocycloalkyl$(C_1-C_6)$alkyl, $(C_6-C_{10})$aryl, $(C_6-C_{10})$aryl$(C_1-C_6)$alkyl or $(C_2-C_9)$heteroaryl$(C_1-C_6)$alkyl; wherein the alkyl, alkenyl, alkynyl, cycloalkyl, heterocycloalkyl, aryl and heteroaryl groups are optionally substituted by one to three substituents independently selected from halo, $(C_1-C_3)$alkoxy, hydroxy, nitro, cyano, $(C_6-C_{10})$aryl, $(C_2-C_9)$heteroaryl, $R^8R^9N$, $R^8C(O)$, $R^8C(O)O$, $R^8OC(O)$, $R^8C(O)NH$, $R^8NHC(O)$, $R^8R^9NC(O)$ or $R^8OC(O)_2$, wherein $R^8$ and $R^9$ are each independently hydrogen, $(C_1-C_6)$alkyl optionally substituted by $(C_6-C_{10})$ aryl or $(C_2-C_9)$heteroaryl; or $R^4$ is $R^{15}N(C_1-C_6)$alkyl wherein $R^{15}$ is hydrogen, $(C_1-C_6)$alkyl, $(C_6-C_{10})$aryl $(C_1-C_6)$alkyl or $(C_2-C_9)$heteroaryl$(C_1-C_6)$alkyl;

X is oxygen or $NOR^{16}$ wherein $R^{16}$ is $(C_1-C_6)$alkyl, $(C_2-C_{12})$alkenyl, $(C_2-C_{12})$alkynyl, $(C_3-C_{10})$cycloalkyl$(C_1-C_6)$alkyl, $(C_2-C_9)$heterocycloalkyl$(C_1-C_6)$alkyl, $(C_6-C_{10})$aryl$(C_1-C_6)$alkyl or $(C_2-C_9)$heteroaryl$(C_1-C_6)$alkyl; wherein the alkyl, alkenyl, alkynyl, cycloalkyl, heterocycloalkyl, aryl and heteroaryl groups are optionally substituted by one to three substituents independently selected from halo, $(C_1-C_3)$alkoxy, hydroxy, nitro, cyano, $(C_6-C_{10})$aryl, $(C_2-C_9)$heteroaryl, $R^8R^9N$, $R^8C(O)$, $R^8C(O)O$, $R^8OC(O)NH$, $R^8NHC(O)$, $R^8R^9NC(O)$ or $R^8OC(O)_2$, wherein $R^8$ and $R^9$ are each independently hydrogen or $(C_1-C_6)$alkyl optionally substituted by $(C_6-C_{10})$aryl or $(C_2-C_9)$heteroaryl;

$R^5$ is hydrogen or methyl;

or $R^3$ and $R^4$ may be taken together with the carbons to which they are attached to form a ring such that the compound is represented by the formula II

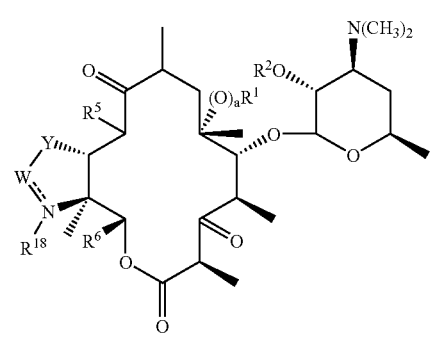

II wherein the dashed line, between the nitrogen and the variable W of formula II, represents an optional double bond;

W is C=O, C=S, $SO_2$ or $C=NR^{10}$ wherein $R^{10}$ is as defined above;

Y is oxygen, sulfur or $NR^{17}$ wherein $R^{17}$ is hydrogen, $R^{19}$, $R^{19}$ O or $R^{19}$ NH wherein $R^{19}$ is hydrogen, $(C_1-C_6)$ alkyl, $(C_2-C_{12})$alkenyl, $(C_2-C_{12})$alkynyl, $(C_3-C_{10})$cycloalkyl$(C_1-C_6)$alkyl, $(C_2-C_9)$heterocycloalkyl$(C_1-C_6)$alkyl, $(C_6-C_{10})$aryl, $(C_6-C_{10})$aryl$(C_1-C_6)$alkyl or $(C_2-C_9)$heteroaryl$(C_1-C_6)$alkyl; wherein the alkyl, alkenyl, alkynyl, cycloalkyl, heterocycloalkyl, aryl and heteroaryl groups are optionally substituted by one to three substituents independently selected from halo, $(C_1-C_3)$alkoxy, hydroxy, nitro, cyano, $(C_6-C_{10})$aryl, $(C_2-C_9)$heteroaryl, $R^8R^9N$, $R^8C(O)$, $R^8C(O)O$, $R^8OC$ (O), R⁸C(O)NH, R⁸NHC(O), R⁸R⁹NC(O) or R₈OC(O)₂ wherein R⁸ and R⁹ are each independently hydrogen, or (C₁–C₆)alkyl optionally substituted by (C₅–C₁₀)aryl or (C₂–C₉)heteroaryl;

R¹⁸ is hydrogen, (C₁–C₆)alkyl, (C₆–C₁₀)aryl, (C₆–C₁₀)aryl(C₁–C₆)alkyl or (C₂–C₉)heteroaryl(C₁–C₆)alkyl; wherein the aryl and heteroaryl groups are optionally substituted by one to three substituents independently selected from halo, (C₁–C₃)alkoxy, hydroxy, nitro, cyano, (C₆–C₁₀)aryl, (C₂–C₉)heteroaryl, R²⁰R²¹N, R²⁰C(O), R²⁰C(O)O, R²⁰OC(O), R²⁰C(O)NH, R²⁰NHC(O), R²⁰R²¹NC(O), and R²⁰OCO₂ wherein R²⁰ and R²¹ are each independently hydrogen, or (C₁–C₆)alkyl optionally substituted by (C₆–C₁₀)acyl or (C₅–C₁₀)aryl or (C₂–C₉)heteroaryl;

R⁶ is hydrogen, (C₁–C₆)alkyl, (C₂–C₆)alkenyl, (C₂–C₆)alkynyl, (C₁–C₆)alkoxy(C₁–C₆)alkyl or (C₁–C₆)alkylthio(C₁–C₆)alkyl wherein the alkyl, alkenyl, alkynyl or alkoxy groups are optionally substituted by one to three substituents independently selected from hydroxy and halo; or R⁶ is (C₃–C₁₀)cycloalkyl or (C₅–C₁₀)cycloalkenyl optionally substituted by (C₁–C₆)alkyl or halo; or R⁶ is (C₂–C₈)heterocycloalkyl or (C₂–C₉)heteroaryl optionally substituted by (C₁–C₆)alkyl, (C₂–C₈)alkenyl, (C₂–C₈)alkynyl, (C₃–C₁₀)cycloalkyl, (C₅–C₁₀)cycloalkenyl or aryl wherein the aryl group is optionally substituted by alkyl, (C₁–C₆)alkoxy or halo;

with the proviso that at least one of R¹⁷ or R¹⁸ is hydrogen;

with the proviso that when the dashed line between positions 10 and 11 represents a double bond, R⁴ is hydrogen; and with the proviso that when a is zero, R¹ is hydrogen.

2. A compound according to claim 1, wherein a is 1 and R¹ is (C₁–C₁₀)alkyl.

3. A compound according to claim 1, wherein R² is hydrogen.

4. A compound according to claim 1, wherein R³ is N₃, R¹⁰NH, R₁₀C(O)NH, R¹⁰NHC(O)NH or R₁₀NHNHC(O)NH.

5. A compound according to claim 1, wherein R⁴ is hydrogen, R¹⁴NH or R¹⁴S.

6. A compound according to claim 1, wherein R⁶ is ethyl.

7. A compound according to claim 1, wherein W is C=O and Y is NR¹⁷.

8. A compound according to claim 1, wherein a is 1; R¹ is (C₁–C₁₀)alkyl; R² is hydrogen; R³ is N₃, R¹⁰NH, R¹⁰C(O), R₁₀NHC(O)NH or R₁₀NHNHC(O)NH; R⁴ is hydrogen, R¹⁴NH or R¹⁴S and R⁶ is ethyl.

9. A compound according to claim 1, wherein a is 1; R¹ is (C₁–C₁₀)alkyl; R² is hydrogen; R³ and R⁴ are taken together with the carbons to which they are attached to form a ring such that the compound is represented by formula II; W is C=O and Y is NR¹⁷.

10. A compound according to claim 1, wherein said compound is selected from the group consisting of:

11,12-Dideoxy-3-de((2,6-dideoxy-3-C-methyl-3-O-methyl-α-L-ribohexopyranosyl)oxy)-6-O-methyl-12,11-(iminocarbonyl(2-(3-(4-quinolinyl)propyl)hydrazono))-3-oxoerythromycin;

11,12-Dideoxy-10,11-didehydro-3-de((2,6-dideoxy-3-C-methyl-3-O-methyl-α-L-ribohexopyranosyl)oxy)-6-O-methyl-12-iminocarbonyl((4-(4-(3-pyridinyl)-1H-imidazol-1-yl)butylimino))-3-oxoerythromycin;

11,12-Dideoxy-11,12-didehydro-3-de((2,6-dideoxy-3-C-methyl-3-O-methyl-α-L-ribohexopyrano-5yl)oxy)-6-O-methyl-10-iminocarbonyl((4-(4-(3-pyridinyl)-(H-imidazol-1-yl)butylimino))-3-oxoerythiomycin;

11-Deoxy-10,11-didehydro-3-de((2,6-dideoxy-3-C-methyl-3-O-methyl-α-L-ribohexopyranosyl)-oxy)-6-O-methyl-3-oxoerythromycin-1,2-enol-1,12-cyclicether-2'-acetate;

11-Deoxy-10,11-didehydro-3-de((2,6-dideoxy-3-C-methyl-3-O-methyl-α-L-ribohexopyranosyl)-oxy)-6-O-methyl-8-epi-3-oxoerythromycin-1,2-enol-1,12-cyclicether-2'-acetate;

11,12-Dideoxy-10,11-didehydro-3-de((2,6-dideoxy-3-C-methyl-3-O-methyl-3-O-methyl-α-L-ribohexopyranosyl)oxy)-12-9-azido-6-O-methyl-3-oxoerythromycin-2'-acetate;

11,12-Dideoxy-10,11-didehydro-3-de((2,6-dideoxy-3-C-methyl-3-O-methyl-α-L-ribohexopyranosyl)oxy)-12-β-azido-6-O-methyl-3-oxo-8-epierythromycin-2'-acetate;

11,12-Dideoxy-10,11-didehydro-3-de((2,6-dideoxy-3-C-methyl-3-O-methyl-α-L-ribohexopyranosyl)oxy)-12-β-amino-6-O-methyl-3-oxoerythromycin-2'-acetate;

11,12-Dideoxy-10,11-didehydro-3-de((2,6-dideoxy-3-C-methyl-3-O-methyl-α-L-ribohexopyranosyl)oxy)-12-β-amino-6-O-methyl-3-oxo-8-erythromycin-2'-acetate;

11,12-Dideoxy-10,11-didehydro-3-de((2,6-dideoxy-3-C-methyl-3-O-methyl-α-L-ribohexopyranosyl)oxy)-12-β-acetamino-6-O-methyl-3-oxoerythromycin-2'-acetate;

11,12-Dideoxy-11,12-dehydro-3-de((2,6-dideoxy-3-C-methyl-3-O-methyl-α-L-ribohexopyranosyl)oxy)-10-β-azido-6-O-methyl-3-oxoerythromycin-2'-acetate;

11,12-Dideoxy-11,12-dehydro-3-de((2,6-dideoxy-3-C-methyl-3-O-methyl-α-L-ribohexopyranosyl)oxy)-10-β-amino-6-O-methyl-3-oxoerythromycin-2'-acetate;

11,12-Dideoxy-11,12-dehydro-3-de((2,6-dideoxy-3-C-methyl-3-O-methyl-α-L-ribohexopyranosyl)oxy)-10-β-acetamino-6-O-methyl-3-oxoerythromycin-2'-acetate;

11,12-Dideoxy-3-de((2,6-dideoxy-3-C-methyl-3-O-methyl-α-L-ribohexopyranosyl)oxy)-6-O-methyl-3-oxo-12,11-(iminocarbonylhydrazono)erythromycin-2'-acetate;

11,12-Dideoxy-11,12-dehydro-3-de((2,6-dideoxy-3-C-methyl-3-O-methyl-α-L-ribohexopyranosyl)oxy)-10-β-iminocarbonyhydrazono-6-O-methyl-3-oxo-erythromycin-2'-acetate;

11,12-Dideoxy-10,11-didehydro-3-de((2,6-dideoxy-3-C-methyl-3-O-methyl-α-L-ribohexopyranosyl)oxy)-12-β-isothiocyanato-6-O-methyl-3-oxoerythromycin-2'-acetate;

11,Deoxy-10,11-didehydro-3-de((2,6-dideoxy-3-C-methyl-3-O-methyl-α-L-ribohexopyranosyl)oxy)-12-β-propagyloxy-6-O-methyl-3-oxoerythromycin-2'-acetate;

11-Deoxy-10,11-didehydro-3-de((2,6-dideoxy-3-C-methyl-3-O-methyl-α-L-ribohexopyranosyl)oxy)-6-O-methyl-11-nitromethyl-3-oxoerythromycin-1,2-enol-1,12-cyclicether-2'-acetate; and 11-Deoxy-10,11-didehydro-3-de((2,6-dideoxy-3-C-methyl-3-O-methyl-α-L-ribohexopyranosyl)oxy)-6-O-methyl-11-nitromethyl-8-epi-3-oxoerythromycin-1,2-enol-1,12-cyclicether-2'-acetate.

11. A pharmaceutical composition for the treatment of a disorder selected from a bacterial infection, a protozoal infection, and a disorder related to a bacterial infection or protozoal infection in a mammal, fish, or bird which comprises a therapeutically effective amount of a compound of claim 1 and a pharmaceutically acceptable carrier.

12. The pharmaceutical composition of claim 11 wherein said disorder is pneumonia, otitis media, sinusitis, bronchitis, tonsillitis, or mastoiditis related to infection by *Streptococcus pneumoniae, Haemophilus influenzae, Moraxella catarrhalis, Staphylococcus aureus,* or *Peptostreptococcus* spp.; pharynigitis, rheumatic fever, or glomerulonephritis related to infection by *Streptococcus pyogenes*, Groups C and G streptococci, *Clostridium diptheriae,* or *Actinobacillus haemolyticum*; a respiratory tract infections related to infection by *Mycoplasma pneumoniae, Legionella pneumophila, Streptococcus pneumoniae, Haemophilus influenzae,* or *Chlamydia pneumoniae*; uncomplicated skin or soft tissue infection, abscess or osteomyelitis, or puerperal fever related to infection by *Staphylococcus aureus*, coagulase-positive staphylococci (i.e., *S. epidermidis, S. hemolyticus,* etc.), *Streptococcus pyogenes, Streptococcus agalactiae,* Streptococcal groups C–F (minute-colony streptococci), viridans streptococci, *Corynebactedium minutissimum, Clostridium* spp., or *Bartonella henselae*; uncomplicated acute urinary tract infection related to infection by *Staphylococcus saprophyticus* or *Enterococcus* spp.; urethritis, or cervicitis; a sexually transmitted disease related to infection by *Chlamydia trachomatis, Haemophilus ducreyi, Treponema pallidum, Ureaplasma urealyticum,* or *Neiserria gonorrheae*; toxin disease related to infection by *S. aureus* (food poisoning or toxic shock syndrome), or Groups A, B, and C streptococci; ulcer related to infection by *Helicobacter pylori*; systemic febrile syndrome related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; atherosclerosis or cardiovascular disease related to infection by *Helicobacter pylori* or *Chlamydia pneumoniae*; bovine respiratory disease related to infection by *P. haemolytica, P. multocida, Mycoplasma bovis,* or *Bordetella* spp.; cow enteric disease related to infection by *E. coli* or protozoa; dairy cow mastitis related to infection by *Staph. aureus, Strep. uberis, Strep. agalactiae, Strep. dysgalactiae, Klebsiella* spp., *Corynebacterium,* or *Enterococcus* spp.; swine respiratory disease related to infection by *A. pleuro., P. multocida,* or *Mycoplasma* spp.; swine enteric disease related to infection by *E. coli, Lawsonia intracellularis, Salmonella,* or *Serpulina hyodysinteriae*; cow footrot related to infection by *Fusobacterium* spp.; cow metritis related to infection by *E. coli*; cow hairy warts related to infection by *Fusobactedium necrophorum* or *Bacteroides nodosus*; cow pink-eye related to infection by *Moraxella bovis*; cow premature abortion related to infection by protozoa; urinary tract infection in a dog or cat related to infection by *E. coli*; skin or soft tissue infection in a dog or cat related to infection by *Staph. epidermidis, Staph. intermedius, coagulase neg. Staph.* or *P. multocida*; or dental or mouth infection in a dog or cat related to infection by *Alcaligenes* spp., *Bacteroides* spp., *Clostridium* spp., *Enterobacter* spp., *Eubacterium, Peptostreptococcus, Porphyromonas,* or *Prevotella*.

13. A method of treating a disorder selected from a bacterial infection, a protozoal infection, and a disorder related to a bacterial infection or protozoal infection in a mammal, fish, or bird which comprises administering to said mammal, fish or bird a therapeutically effective amount of a compound of claim 1.

14. The method of claim 13, wherein said disorder is pneumonia, otitis media, sinusitis, bronchitis, tonsillitis, or mastoiditis related to infection by *Streptococcus pneumoniae, Haemophilus influenzae, Moraxella catarrhalis, Staphylococcus aureus,* or *Peptostreptococcus* spp.; pharynigitis, rheumatic fever, or glomerulonephritis related to infection by *Streptococcus pyogenes*, Groups C and G streptococci, *Clostridium diptheriae,* or *Actinobacillus haemolyticum*; a respiratory tract infections related to infection by *Mycoplasma pneumoniae, Legionella pneumophila, Streptococcus pneumoniae, Haemophilus influenzae,* or *Chlamydia pneumoniae*; uncomplicated skin or soft tissue infection, abscess or osteomyelitis, or puerperal fever related to infection by *Staphylococcus aureus*, coagulase-positive staphylococci (i.e., *S. epidermidis, S. hemolyticus,* etc.), *Streptococcus pyogenes, Streptococcus agalactiae,* Streptococcal groups C–F (minute-colony streptococci), viridans streptococci, *Corynebacterium minutissimum, Clostridium* spp., or *Bartonella henselae*; uncomplicated acute urinary tract infection related to infection by *Staphylococcus saprophyticus* or *Enterococcus* spp.; urethritis, or cervicitis; a sexually transmitted disease related to infection by *Chlamydia trachomatis, Haemophilus ducreyi, Treponema pallidum, Ureaplasma urealyticum,* or *Neiserria gonorrheae*; toxin disease related to infection by *S. aureus* (food poisoning or toxic shock syndrome), or Groups A, B, and C streptococci; ulcer related to infection by *Helicobacter pylori*; systemic febrile syndrome related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; atherosclerosis or cardiovascular disease related to infection by *Helicobacter pylori* or *Chlamydia pneumoniae*; bovine respiratory disease related to infection by *P. haemolytica, P. multocida, Mycoplasma bovis,* or *Bordetella* spp.; cow enteric disease related to infection by *E. coli* or protozoa; dairy cow mastitis related to infection by *Staph. aureus, Strep. uberis,* Strep. agalactiae, Strep. dysgalactiae, *Klebsiella* spp., *Corynebacterium,* or *Enterococcus* spp.; swine respiratory disease related to infection by *A. pleuro.*, *P. multocida*, or *Mycoplasma* spp.; swine enteric disease related to infection by *E. coli*, *Lawsonia intracellularis*, *Salmonella*, or *Serpulina hyodysinteriae*; cow footrot related to infection by *Fusobacterium* spp.; cow metritis related to infection by *E. coli*; cow hairy warts related to infection by *Fusobacterium necrophorum* or *Bacteroides nodosus*; cow pink-eye related to infection by *Moraxella bovis*; cow premature abortion related to infection by protozoa; urinary tract infection in a dog or cat related to infection by *E. coli*; skin or soft tissue infection in a dog or cat related to infection by *Staph. epidermidis*, *Staph. intermedius*, *coagulase neg. Staph.* or *P. multocida*; or dental or mouth infection in a dog or cat related to infection by *Alcaligenes* spp., *Bacteroides* spp., *Clostridium* spp., *Enterobacter* spp., *Eubacterium*, *Peptostreptococcus*, *Porphyromonas*, or *Prevotella*.

* * * * *